(12) United States Patent
Jung et al.

(10) Patent No.: US 10,507,604 B2
(45) Date of Patent: Dec. 17, 2019

(54) NANOTRANSFER PRINTING METHOD AND SURFACE-ENHANCED RAMAN SCATTERING SUBSTRATE, SURFACE-ENHANCED RAMAN SCATTERING VIAL AND SURFACE-ENHANCED RAMAN SCATTERING PATCH MANUFACTURED USING THE SAME

(71) Applicant: Korea Advanced Institute of Science and Technology, Daejeon (KR)

(72) Inventors: Yeon Sik Jung, Daejeon (KR); Jae Won Jeong, Daejeon (KR); Kwang Min Baek, Daejeon (KR); Jong Min Kim, Daejeon (KR); Tae Won Nam, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 560 days.

(21) Appl. No.: 14/884,529

(22) Filed: Oct. 15, 2015

(65) Prior Publication Data
US 2016/0202123 A1 Jul. 14, 2016

(30) Foreign Application Priority Data

Oct. 29, 2014 (KR) .......................... 10-2014-0148502
Nov. 14, 2014 (KR) .......................... 10-2014-0159159
Sep. 14, 2015 (KR) .......................... 10-2015-0129896

(51) Int. Cl.
*B29C 39/02* (2006.01)
*C23C 14/04* (2006.01)
*B29L 31/00* (2006.01)

(52) U.S. Cl.
CPC ............ *B29C 39/026* (2013.01); *C23C 14/04* (2013.01); *B29L 2031/757* (2013.01)

(58) Field of Classification Search
None
See application file for complete search history.

(56) References Cited

U.S. PATENT DOCUMENTS

2003/0151895 A1* 8/2003 Zuo .......................... F28F 13/10
  361/699
2009/0295364 A1* 12/2009 Cao .......................... B82Y 30/00
  324/71.1

(Continued)

FOREIGN PATENT DOCUMENTS

EP  1731961 A1  12/2006
JP  2007-501391 A  1/2007

(Continued)

OTHER PUBLICATIONS

Abu Hatab et al., "Surface-Enhanced Raman Spectroscopy Substrates Created via Electron Beam Lithography and Nanotransfer Printing", ACS Nano, vol. 2, No. 2, (2008).*

(Continued)

*Primary Examiner* — James M Mellott
(74) *Attorney, Agent, or Firm* — Marshall, Gerstein & Borun LLP

(57) ABSTRACT

A nanotransfer printing method, including the steps of coating a polymer thin film on a template substrate where a surface pattern is formed, fabricating the polymer thin film into a thin-film replica mold by using the polymer thin film and an adhesive film, forming nanostructures on the thin-film replica mold, selectively weakening an adhesive force between the adhesive film and the thin-film replica mold, and transferring the nanostructures into a target object, is provided.

15 Claims, 23 Drawing Sheets

(56) References Cited

U.S. PATENT DOCUMENTS

| | | | |
|---|---|---|---|
| 2011/0140209 A1 | 6/2011 | Wang et al. | |
| 2012/0276438 A1* | 11/2012 | Saka | C01B 25/45 429/144 |
| 2014/0041217 A1 | 2/2014 | Ito et al. | |

FOREIGN PATENT DOCUMENTS

| | | |
|---|---|---|
| KR | 2011-0134175 A | 12/2011 |
| KR | 101449850 B1 | 10/2014 |
| WO | WO-2004/027460 A2 | 4/2004 |
| WO | WO-2010/056258 A1 | 5/2010 |
| WO | WO-2014/011954 A1 | 1/2014 |

OTHER PUBLICATIONS

Su et al., "Tunable and Augmented Plasmon Resonances of Au/SiO2/Au Nanodisks", Applied Physics Letters, vol. 88, No. 063118, (2006).*

Jeong et al., "Solvent-Vapor-Assisted Nanotransfer Printing with Sub-10-nm Resolution", Proceeding Papers: The 114th General Meeting of the Korean Chemical Society, (Oct. 15, 2014).*

Jeong, "Ultrahigh-Resolution Nano-Transfer Printing Applicable to Applicable to a Broad Range of Surfaces", Proceeding Papers: The 114th General Meeting of the Korean Chemical Society, (Oct. 15, 2014), [Abstract Only].*

C. Schaper, Patterned Transfer of Metallic Thin Film Nanostructures by Water-Soluble Polymer Templates, Nano Letters, vol. 3, No. 9, 1305-1309, Jul. 26, 2003.*

Jeong et al., "Highly reliable nanotransfer printing with sub-10-nm resolution via solvent-vapor-assisted adhesion switching," Korea Advanced Institute of Science and Technology, Nov. 17, 2014.

Jeong et al., "High-resolution nanotransfer printing applicable to diverse surfaces via interface-targeted adhesion switching," Nature Communications, Macmillan Publishers Limited, Nov. 10, 2014.

Jeong et al., "Solvent-vapor-assisted nanotransfer printing with sub-10-nm resolution," Abstract published Oct. 15, 2014.

Jeong et al., "Solvent-vapor-assisted Nanotransfer Printing with Sub-10-nm Resolution," published Oct. 15, 2014.

International Search Report issued in PCT Patent Application No. PCT/KR2015/011082 dated Feb. 29, 2016.

Extended European Search Report issued in European Patent Application No. 15191672.3 dated Mar. 29, 2016.

Jeong et al., "High-resolution nanotransfer printing applicable to diverse surfaces via interface-targeted adhesion switching," *Nature Communications*, vol. 5 (Nov. 2014).

* cited by examiner

NANOTRANSFER PRINTING METHOD AND SURFACE-ENHANCED RAMAN SCATTERING SUBSTRATE, SURFACE-ENHANCED RAMAN SCATTERING VIAL AND SURFACE-ENHANCED RAMAN SCATTERING PATCH MANUFACTURED USING THE SAME

CROSS-REFERENCE TO RELATED APPLICATION(S)

This application claims the benefit under 35 U.S.C. § 119(a) of a Korean patent application filed on Oct. 29, 2014 in the Korean Intellectual Property Office and assigned Serial number 10-2014-0148502, a Korean patent application filed on Nov. 14, 2014 in the Korean Intellectual Property Office and assigned Serial number 10-2014-0159159, and a Korean patent application filed on Sep. 14, 2015 in the Korean Intellectual Property Office and assigned Serial number 10-2015-0129896, the entire disclosure of which is hereby incorporated by reference.

TECHNICAL FIELD

The present disclosure relates to a nanotransfer printing method and a Surface-Enhanced Raman Scattering substrate (SERS), a surface-enhanced Raman scattering vial and a surface-enhanced Raman scattering patch manufactured using the method, and more particularly, to technology of manufacturing an SERS substrate, an SERS vial, or an SERS patch by duplicating a surface pattern of a template substrate with a polymer thin film and manufacturing a thin film replica, by forming nanostructures on the thin film replica, and by transferring the nanostructures into various target objects.

BACKGROUND

When light is projected to specific molecules, inelastic scattering occurs between light and the molecules in the probability of 1/1,000,000 and the light partially loses its energy by the constituents and structures of the molecules to cause a variation in wavelength. The Raman spectroscopy is developed to obtain information about constituents and structures of target molecules, using such a mechanism, i.e., by projecting a mono-wavelength laser and by analyzing the intensity of reflected light (Raman signal) in wavelength bands. The Raman spectroscopy is nowadays rising as the new-generation analyzing technology by virtue of its rapidness, accuracy, and capability of nondestructive analysis.

However, as the Raman spectroscopy makes inelastic scattering occur in very low probability of 1/1,000,000, intensity of reflected light is very weak. Therefore, if an amount of molecules to be analyzed is minutely little, the Raman spectroscopy is regarded as being unsuitable for inspecting trace materials because an obtained Raman signal cannot be differentiated from a background signal.

To solve such low signal intensity, there has been proposed a methodological technique using an effect of Surface-Enhanced Raman Scattering (SERS). The SERS is the technology of increasing a Raman signal, which is obtained from molecules absorbed on a nanostructured surface, $10^3$ to $10^{15}$ times by greatly increasing intensity of light by locally focusing the projected light through a Surface Plasmon Resonance (SPR) effect of the nanostructured surface such as Au or Ag.

Nanostructures utilizing such an SERS effect may be generally disposed on a plane substrate. Nanostructures may be manufactured in a form of SERS substrate to perform an analysis by laser after spreading trace molecules, which are to be analyzed, on the surface of the substrate through a suitable process such as drop casting. An SERS substrate should be high in signal enhancement effect to allow an analysis of trace molecules, superior in signal equality and reproducibility due to a high uniformity rate of nanostructures on the substrate, and inexpensive in manufacturing cost because of difficult recycling.

General SERS substrates have been manufactured, roughly, in two methods. One is using a photolithography process such as photolithography or E-beam lithography to form a pattern and to deposit Au or Ag for nanostructures, accomplishing topological uniformity, but disadvantageous with a high price of lithography equipment for pattering and with a high processing cost thereof. The other one is compounding nanostructures into a solution and then scattering the solution on a substrate to manufacture an SERS substrate, having a simple and inexpensive process, but disadvantageous with remarkably low signal equality and reproducibility because the nanostructures are randomly distributed on the substrate.

Therefore, to widely utilizing the Raman spectroscopy using SERS in analyzing trace molecules, there is a need of technology for manufacturing an SERS substrate having high signal enhancement capability, superior signal equality and reproducibility, and low manufacturing cost.

SUMMARY

Aspects of the present disclosure are to address at least the above-mentioned problems and/or disadvantages and to provide at least the advantages described below. Accordingly, an aspect of the present disclosure is to provide a high-performance SERS device (SERS substrate, SERS vial and/or SERS patch) with high signal enhancement capability, and superior signal equality and reproducibility in a low cost by performing, instead of a lithography process, a nanotransfer printing process which forms and transfers nanostructures into a target object.

Additionally, another aspect of the present disclosure is to provide a method of using a nanotransfer printing process having high resolution without pretreatment and controlling an adhesive force during a process of manufacturing an SERS device.

Additionally, another aspect of the present disclosure is to provide an SERS device in which nanostructured thin films are stacked to allow a coupling effect between the nanostructured thin films to secure a high Raman signal.

In accordance with an aspect of the present disclosure, a nanotransfer printing method may include the steps of coating a polymer thin film on a template substrate where a surface pattern is formed, fabricating the polymer thin film into a thin-film replica mold by using the polymer thin film and an adhesive film, forming nanostructures on the thin-film replica mold, selectively weakening an adhesive force between the adhesive film and the thin-film replica mold, and transferring the nanostructures into a target object.

The step of forming the nanostructures may include a step of depositing a functional material on the thin-film replica mold through an angled deposition.

The step of depositing the functional material on the thin-film replica mold may include a step of depositing the functional material on the thin-film replica mold, which is slanted to have a specific angle with a surface prepared for the deposition of the thin-film replica mold in a direction of the deposition, to deposit the functional material only on protruded parts of the surface prepared for the deposition of the thin-film replica mold.

The template substrate may be formed with a rugged type of the surface pattern through a reactive ion etching process and a patterning process including at least one of photolithography, block copolymer self-assembling lithography, or E-beam lithography.

The step of coating the polymer thin film may include one of steps of spreading a monolayered thin film and forming the polymer thin film, and sequentially spreading a first thin film and a second thin film and forming the polymer thin film as a multilayered thin film.

The step of coating the polymer thin film may include a step of spreading the polymer through at least one of spin coating, deep coating, or spray coating.

The step of fabricating the polymer thin film into the thin-film replica mold may include steps of uniformly attaching the adhesive film to a side of the polymer thin film, and separating the polymer thin film, to which the adhesive film is attached, from the template substrate.

The step of selectively weakening the adhesive force between the adhesive film and the thin-film replica mold may include a step of injecting an organic solvent vapor between the adhesive film and the thin-film replica mold to reduce interfacial detachment energy.

The step of injecting the organic solvent vapor between the adhesive film and the thin-film replica mold may include one of steps of touching a polymer pad, which contains an organic solvent, to the thin-film replica mold and providing the organic solvent vapor, and providing the organic solvent vapor that is evaporated from a liquid organic solvent.

The organic solvent may be similar to the polymer thin film, which composes the thin-film replica mold, and the adhesive film in solubility parameter within a specific range.

The step of transferring the nanostructures into the target object may include steps of touching the adhesive film and the thin-film replica mold, in which the nanostructures are formed, to a polymer pad to make the nanostructures meet the polymer pad, separating the thin-film replica mold and the adhesive film from the polymer film to leave the nanostructures in the polymer pad, touching the polymer pad, in which the nanostructures remain, to the target object to make the nanostructures meet the target object, and separating the polymer pad from the target object to make the nanostructures transferred into the target object.

The step of separating the thin-film replica mold and the adhesive film from the polymer pad may include steps of separating the adhesive film from the thin-film replica mold that is touched to the polymer pad, and using an organic solvent to remove the thin-film replica mold that is touched to the polymer pad.

The step of transferring the nanostructures into the target object may include steps of touching the adhesive film and the thin-film replica mold, in which the nanostructures are formed, to the target object to make the nanostructures meet the target object, and separating the thin-film replica mold and the adhesive film from the target object to make the nanostructures transferred into the target object.

The steps of separating the thin-film replica mold and the adhesive film from the target object may include separating the adhesive film from the thin-film replica mold that is touched to the target object, and using an organic solvent to remove the thin-film replica mold that is touched to the target object.

The nanotransfer printing method may further include a step of repeating the step of transferring the nanostructures into the target object to generate a three-dimensional nano structured SERS device with a stack of a plurality of layers.

The step of transferring the nanostructures into the target object may further include a step of transferring the nanostructures into a metallic thin film.

In accordance with another aspect of the present disclosure, a surface-enhanced Raman scattering (SERS) device may use nanostructures. The nanostructures may be formed by a process including the steps of coating a polymer thin film on a template substrate where a surface pattern is formed, fabricating the polymer thin film into a thin-film replica mold by using the polymer thin film and an adhesive film, forming the nanostructures on the thin-film replica mold, selectively weakening an adhesive force between the adhesive film and the thin-film replica mold, and transferring the nanostructures into a target object.

The SERS device using the nanostructures may be formed in a type of substrate, vial, or patch according to the target object into which the nanostructures are transferred and may be used for analyzing ingredients of a material.

The SERS device using the nanostructures may include at least one of an SERS substrate, an SERS vial, or an SERS patch.

The SERS device using the nanostructures may include a three-dimensional structure having the nanostructures which are stacked in plurality by repeating the process.

The step of transferring the nanostructures into the target object may include a step of transferring the nanostructures into a metallic thin film, and the SERS device using the nanostructures may include a hybrid structure in which the nanostructures are transferred into the metallic thin film.

According to embodiments of the present disclosure, it may be accomplishable to provide a high-performance SERS device (SERS substrate, SERS vial and/or SERS patch) with high signal enhancement capability, and superior signal equality and reproducibility in a low cost by performing, instead of a lithography process, a nanotransfer printing process which forms and transfers nanostructures into a target object.

Additionally, it may be accomplishable to provide a method of using a nanotransfer printing process having high resolution without pretreatment and controlling an adhesive force during a process of manufacturing an SERS device.

Accordingly, it may be permissible to manufacture SERS services in various forms by performing a nanotransfer printing process into various types of target objects.

Additionally, it may be accomplishable to provide an SERS device in which nanostructured thin films are stacked to allow a coupling effect between the nanostructured thin films to secure a high Raman signal.

DETAILED DESCRIPTION

Figure 1:
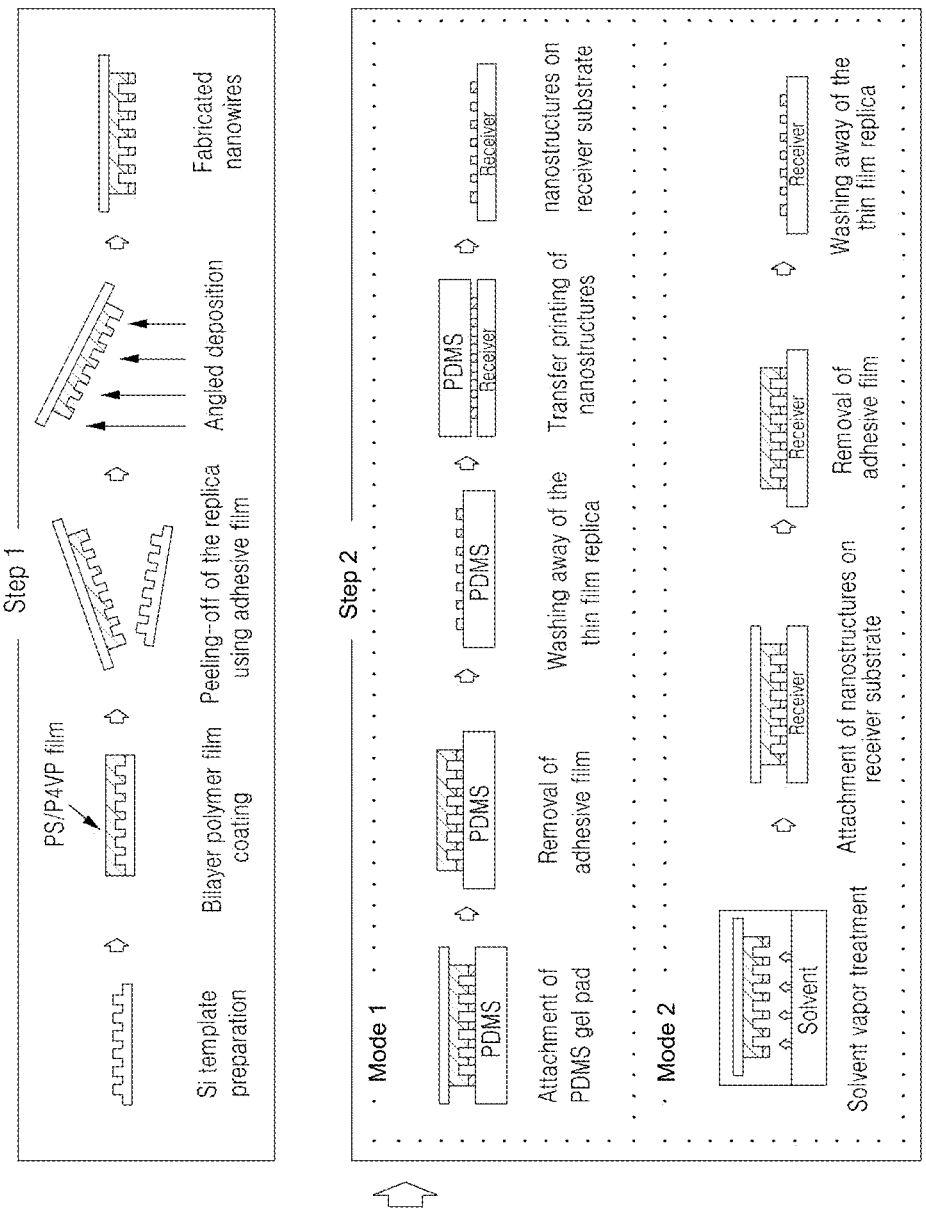
FIG. 1 is a schematic diagram illustrating a processing flow of manufacturing an SERS device using nanotransfer printing according to an embodiment of the present disclosure.

Hereinafter, various embodiments of the present disclosure will be described in conjunction with the accompanying drawings. Various embodiments described herein, however, may not be intentionally confined in specific embodiments, but should be construed as including diverse modifications, equivalents, and/or alternatives. With respect to the descriptions of the drawings, like reference numerals refer to like elements.

The terms used in this specification are just used to properly describe various embodiments of the present disclosure and may be changed according to intentions of users or operators, or may be modifiable according to usual practices of the art. Therefore, the terms used herein may be defined based on the overall definition throughout this specification.

Embodiments of the present disclosure are concerned with technology of manufacturing an SERS device including an SERS substrate, an SERS vial, and an SERS patch, using a nanotransfer printing method which forms and transfers nanostructures into a target object.

According to an embodiment of the present disclosure, after coating a polymer thin film on a template substrate in which a surface pattern is formed and forming a thin-film replica mold from the polymer thin film by using the polymer thin film and an adhesive thin film, nanostructures are formed on the thin-film replica mold and transferred into a target object through nanotransfer printing to result in an SERS device. An SERS device may be manufactured in a form of substrate, vial, or patch according to a target object into which nanostructures are transferred. This feature will be described in conjunction with the accompanying drawings.

FIG. 1 is a schematic diagram illustrating a processing flow of manufacturing an SERS device using nanotransfer printing according to an embodiment.

Referring FIG. 1, a system of manufacturing an SERS device according to an embodiment of the present disclosure (hereinafter, referred to as 'SERS device manufacturing system') may fabricate an SERS device through a Solvent-vapor-injection nanoTransfer Printing (S-nTP) process using an organic solvent vapor.

In detail, an S-nTP process may include two successive steps. A first step may be performed by depositing a polymer thin film on a template substrate in which a surface pattern is formed, forming a thin-film replica mold from the polymer thin film with the polymer thin film and an adhesive film, and thereafter forming nanostructures on the thin-film replica mold.

During this, on the template substrate, a rugged surface pattern may be formed using a Reactive Ion Etching (RIE) process and a patterning process including at least one of photolithography, block copolymer self-assembling lithography, or E-beam lithography.

For example, an SERS device manufacturing system may perform surface etching by an RIE process, after forming a specific-sized surface pattern on a template substrate through a patterning process, and then allow the surface pattern to be rugged. In more detail, for example, an SERS device manufacturing system may fabricate a template substrate through a patterning process of block copolymer self-assembling lithography on a silicon wafer to form ultramicroscopic surface patterns equal to or smaller than 20 nm. This processing feature will be described later in conjunction with FIG. 2A.

An SERS device manufacturing system may coat a polymer thin film by spreading the polymer thin film on a template substrate through at least one of spin coating, deep coating, or spray coating. During this, a polymer spread as a polymer thin film may have a solubility parameter of 20 to 40 Mpa$^{1/2}$, and glass transition temperature higher than the normal temperature 25° C. Accordingly, the polymer may stably retain its solid state at the normal temperature.

Additionally, an SERS device manufacturing system may form a polymer thin film by spreading a monolayered thin film, or by spreading a first thin film and a second thin film in sequence. This processing feature will be described later in conjunction with FIGS. 3A and 3B.

An SERS device manufacturing system may form nanostructures by depositing a functional material through oblique deposition. This processing feature will be described later in conjunction with FIG. 4A.

Once the first step is completed as such, after selectively weakening an adhesive force between an adhesive film and a thin-film replica mold, a second step (S-nTP 2 process) is performed to transfer nanostructures into a target object.

During this, an SERS device manufacturing system may selectively weaken an adhesive force between an adhesive film and a thin-film replica mold, by injecting an organic solvent vapor between the adhesive film and the thin-film replica mold, to reduce interfacial detachment energy.

An S-nTP 2 process may be differently applied thereto, according to a mode of providing an organic solvent vapor, in transferring nanostructures into a target object. For example, an S-nTP 2 process may include different transferring processes in accordance with a first mode which uses a polymer pad containing an organic solvent, and a second mode which uses a liquid organic solvent.

According to the first mode of the S-nTP 2 process, an SERS device manufacturing system may provide an organic solvent vapor by touching a polymer pad, which contains an organic solvent, to a thin-film replica mold. For example, an SERS device manufacturing system may control an adhesive film and a thin-film replica mold, in which nanostructures are formed, to be touched to a polymer pad for a specific time (e.g., 10 to 60 seconds), touching the nanostructures to the polymer pad.

A polymer pad is a kind of pad absorbing an organic solvent and expanding thereby, for example, a polydimetylsiloxane (PDMS) pad, and may be formed through crosslink and separation after mounting a mixture of precursors and a curing agent on a silicon wafer and then heating up the structure. During this, a polymer pad may be formed using a crosslinked polymer which has a solubility parameter ranging from 10 to 40 MPa$^{1/2}$. An organic solvent absorbed in a polymer pad may have a solubility parameter similar to that of a polymer thin film, which composes a thin-film replica mold, and/or that of an adhesive film in a specific range. Additionally, an organic solvent may be used with a single ingredient, or with two or more different ingredients. This processing feature will be further described later in conjunction with FIG. 5.

An organic solvent provided in contact with a thin-film replica mold may be injected between an adhesive film and a thin-film replica mold and weaken an adhesive force between them. If this injection is performed, an SERS device manufacturing system may separate a thin-film replica mold and an adhesive film from a polymer pad to leave nanostructures on the polymer pad. During this, it may be permissible to remove a thin-film replica mold from a polymer pad by using an organic solvent after separating an adhesive film from the polymer pad.

For example, an SERS device manufacturing system may separate only an adhesive film therefrom mold after touching the adhesive film to the thin-film replica mold to make nanostructures meet a polymer pad. Subsequently, the SERS device manufacturing system may remove a thin-film replica mold from a polymer pad by washing the structure with an organic solvent, such as toluene, acetone, or IPA solvent, to leave only nanostructures on the polymer pad, or by precipitating the polymer pad, which is touched to the thin-film replica mold, in an organic solvent. This processing feature will be further described later in conjunction with FIG. 6.

Accordingly, it may be allowable to transfer a polymer pad, in which nanostructures remain, into a target object. For example, an SERS device manufacturing system may separate a polymer pad from a target object to allow nanostructures to be transferred into the target object after touching the polymer pad, in which the nanostructures remain, to the target object (e.g., for 1 to 5 seconds) to make the nanostructures meet the target object.

On the other hand, according to the second step of the S-nTP process, an SERS device manufacturing system may provide an organic solvent vapor which is evaporated from a liquid organic solvent. For example, an SERS device manufacturing system may weaken an adhesive force between an adhesive film and a thin-film replica mold by injecting an organic solvent, which has a solubility parameter similar to that of a polymer thin film composing the thin-film replica mold, and/or similar to that of the adhesive film in a specific range, between the adhesive film and the thin-film replica mold. This processing feature will be further described later in conjunction with FIG. 7.

After performing such a process, an SERS device manufacturing system may touch an adhesive film and a thin film replica (e.g., for 1 to 5 seconds), in which nanostructures are formed, to a target object to make the nanostructures meet the target object. Subsequently, the SERS device manufacturing system may separate the thin film replica and the adhesive film from the target object to allow the nanostructures to be transferred into the target object.

For example, an SERS device manufacturing system may touch a thin-film replica mold to an adhesive film to make nanostructures meet a target object, may separate the adhesive film therefrom, and then may remove the thin-film replica mold from the target object by using an organic solvent. For example in more detail, an SERS device manufacturing system may remove a thin-film replica mold from a target object by washing away the thin-film replica mold with an organic solvent, or by precipitating the target object, which is touched to the thin-film replica mold, in an organic solvent.

As aforementioned, an SERS device may be manufactured through the S-nTP 1 and S-nTP 2 processes which form metallic nanostructures made of Au, Ag, Cu, Ni, Pt, Cr, Co, or Pd and transfer-print the nanostructures into a target object. During this, since a nanotransfer printing process by the S-nTP 1 and S-nTP 2 processes can be applied to a flexible substrate, or a biological surface such as a part of food or body, as well as a general substrate, it may be permissible to manufacture various kinds of SERS devices. These applications will be further described later in conjunction with FIG. 14.

Especially, an SERS device manufacturing system may fabricate a high-performance SERS device having superior signal equality and reproducibility with a high signal enhancement effect by uniformly forming a large area of ultramicroscopic nanostructures, which are scaled equal to or smaller than 20 nm, through a nanotransfer printing process (the S-nTP 1 and S-nTP 2 processes) capable of conducting high resolution without a pretreatment process and controlling an adhesive force, even without any expensive lithography process such as photolithography or E-beam lithography.

Since an area of nanostructures of an SERS device is same with a surface area of a template substrate based thereon, the nanostructures with a large area of nanowired thin films may be implemented in the SERS device as extending the surface area of the template substrate.

Figure 2A:
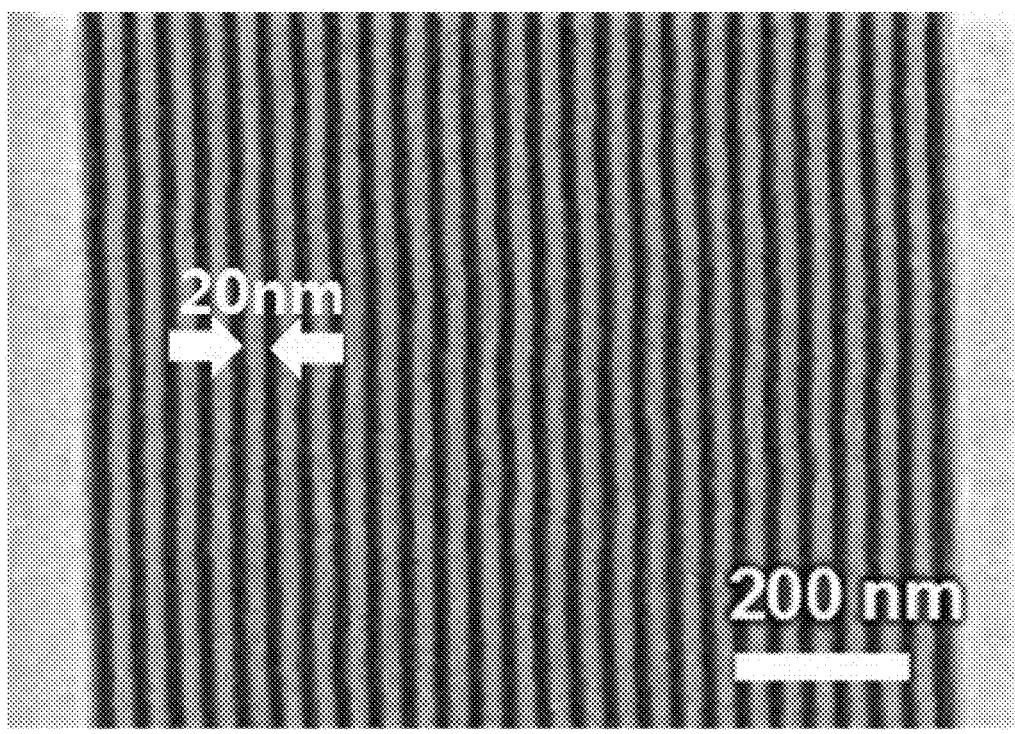
FIG. 2A shows an SEM image on a surface pattern of a template substrate used in a process of manufacturing an SERS device according to an embodiment of the present disclosure.
Figure 2B:
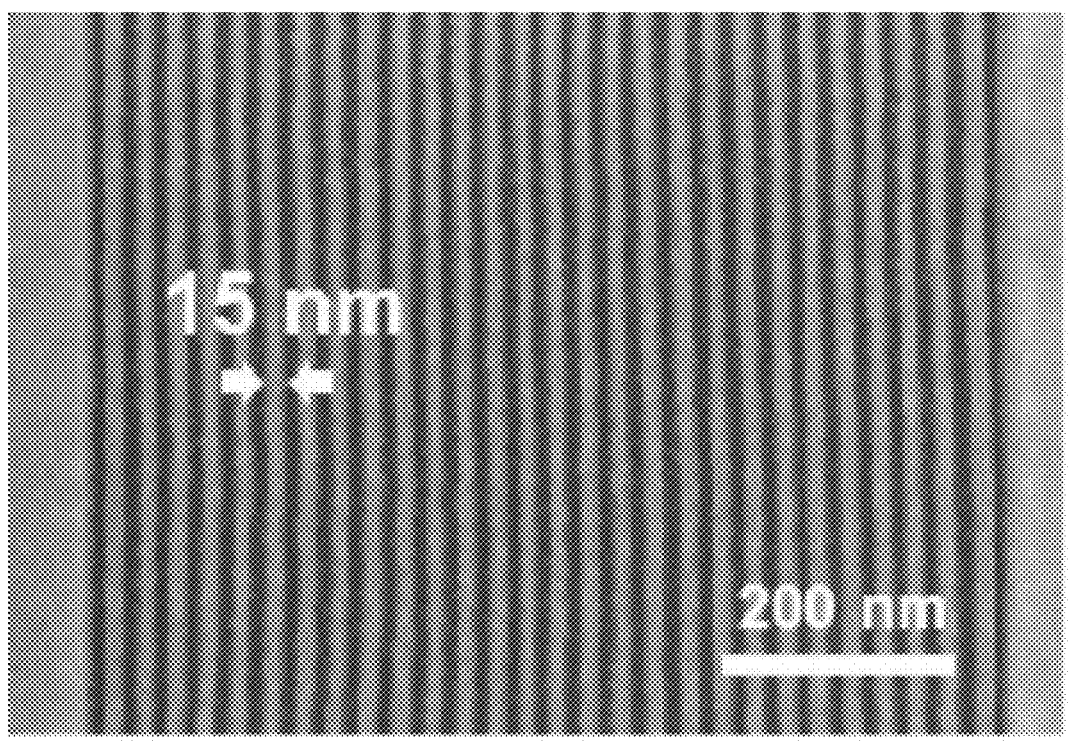
FIG. 2B shows an SEM image on a surface pattern of a template substrate used in a process of manufacturing an SERS device according to another embodiment of the present disclosure.
Figure 2C:
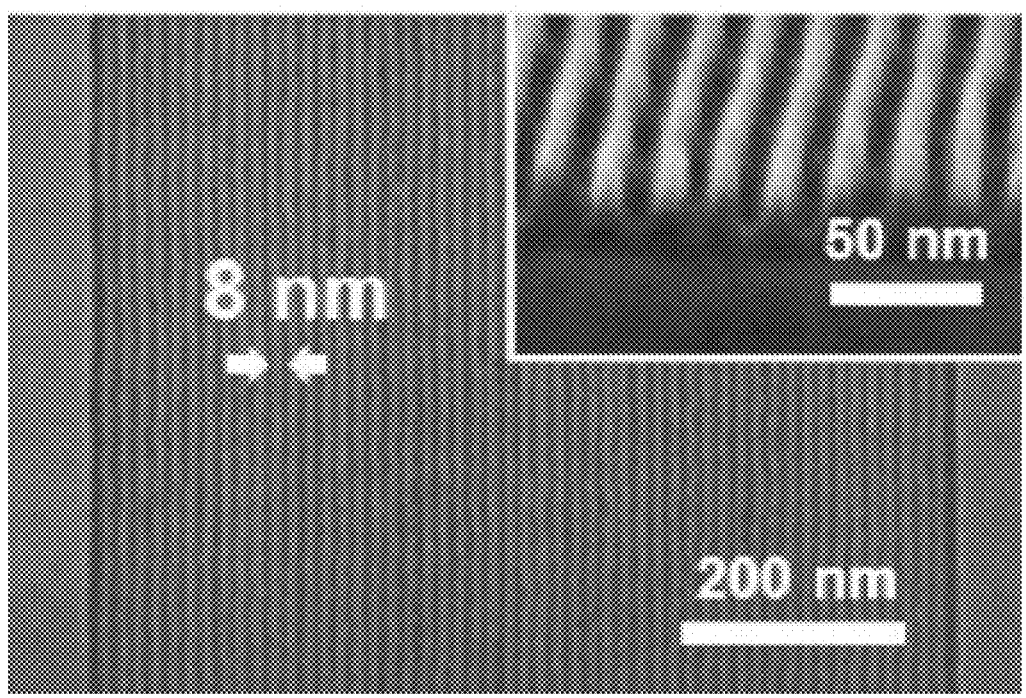
FIG. 2C shows an SEM image on a surface pattern of a template substrate used in a process of manufacturing an SERS device according to still another embodiment of the present disclosure.
Figure 2D:
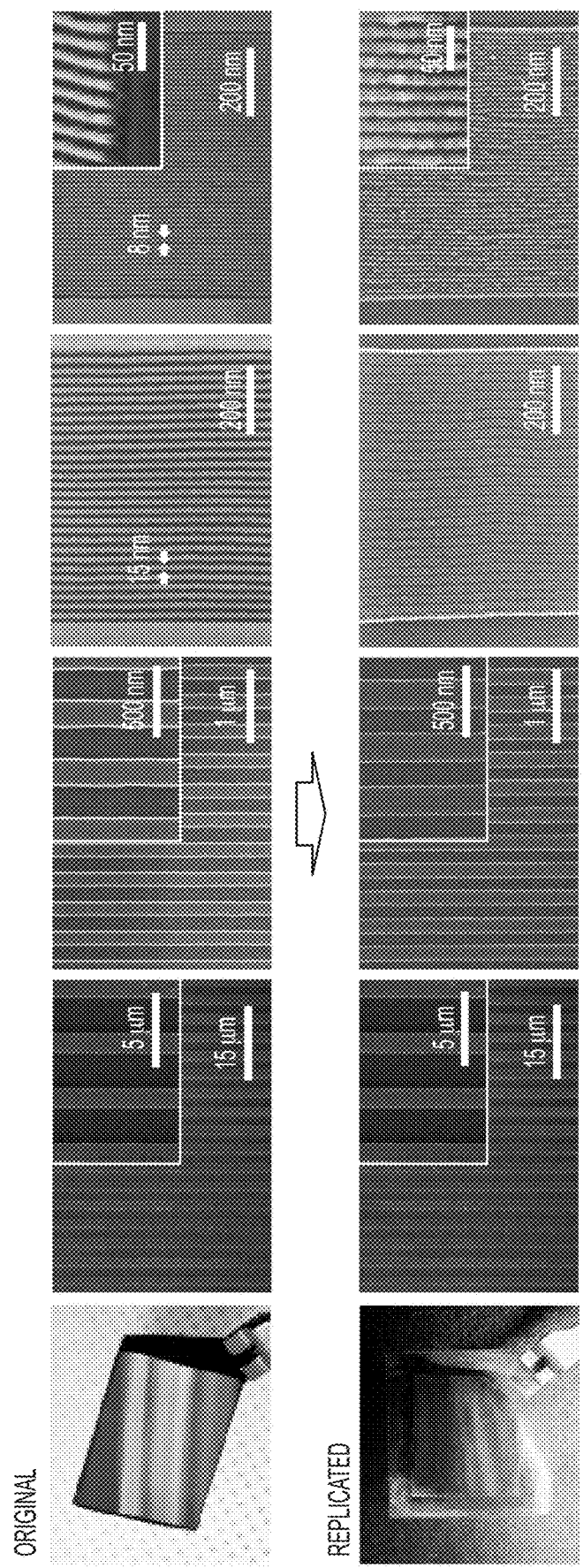
FIG. 2D shows an SEM image on a surface pattern of a template substrate formed through a photolithography process according to an embodiment of the present disclosure.

FIG. 2A shows an SEM image on a surface pattern of a template substrate used in a process of manufacturing an SERS device according to an embodiment, FIG. 2B shows an SEM image on a surface pattern of a template substrate used in a process of manufacturing an SERS device according to another embodiment, FIG. 2C shows an SEM image on a surface pattern of a template substrate used in a process of manufacturing an SERS device according to still another embodiment, and FIG. 2D shows an SEM image on a surface pattern of a template substrate formed through a photolithography process according to an embodiment. The SEM images described hereinafter are taken by Scanning Electron Microscopy (SEM) on scale of 200 nm.

Referring to FIG. 2A, an SERS device manufacturing system according to an embodiment may fabricate a template substrate with a rugged surface pattern of 20-nm line width by performing an RIE process under oxygenic condition after forming a linear surface pattern after self-assembling poly(styrene-b-dimethylsiloxne) (PDMS) block copolymer with a silicon trench substrate having a width of 1 μm to 1 cm and a depth of 1 nm to 1 cm.

Additionally, an SERS device manufacturing system may control the surface of a template substrate to have low surface energy equal to or lower than 30 mJ/m$^2$ by performing a coating process with a PDMS brush polymer or hexamethylene disilazane (HDMS). This is to easily separate a thin-film replica mold from a template substrate in the following process. The surface of a template substrate does not need to be retreated because of its semipermanent usability.

Additionally, referring to FIG. 2B showing an SEM image of a surface pattern of a template substrate used in a process of manufacturing an SERS device according to another embodiment, and referring to FIG. 2C showing an SEM image on a surface pattern of a template substrate used in a process of manufacturing an SERS device according to still another embodiment, an SERS device manufacturing system may even fabricate a template substrate with a rugged surface pattern of line widths in 15 nm and 8 nm, respectively, by performing an RIE process under oxygenic condition after forming a linear surface pattern by self-assembling a PS-PDMS block copolymer in a silicon trench substrate having a width of 1 μm to 1 cm and a depth of 1 nm to 1 cm.

Additionally, an SERS device manufacturing system may perform various patterning processes to fabricate a template substrate which is used for replicating a surface pattern in a process of manufacturing an SERS device. For example, referring to FIG. 2D showing an SEM image on a surface pattern of a template substrate formed through a photolithography process according to an embodiment, an SERS device manufacturing system may form a linear surface pattern with a line width of several hundreds of nanometers or several microns through a photolithography process. However, embodiments of the present disclosure may not be restrictive hereto and an SERS device manufacturing system may from various surface patterns, such as dots or holes, in addition to such a linear surface pattern, through a photolithography process or a block copolymer self-assembling process.

Figure 3A:
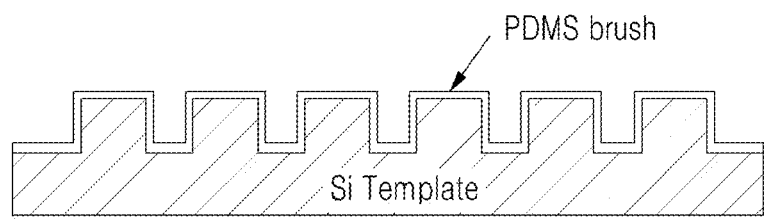
FIG. 3A is a schematic diagram illustrating a processing flow of forming a thin-film replica mold during an SERA manufacturing procedure according to an embodiment of the present disclosure.
Figure 3A:
Figure 3A:
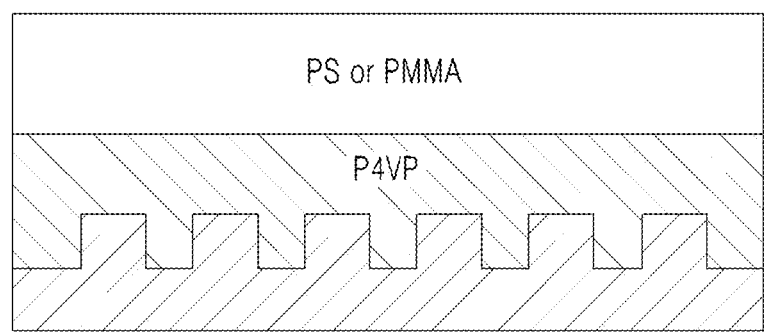
Figure 3A:
Figure 3A:
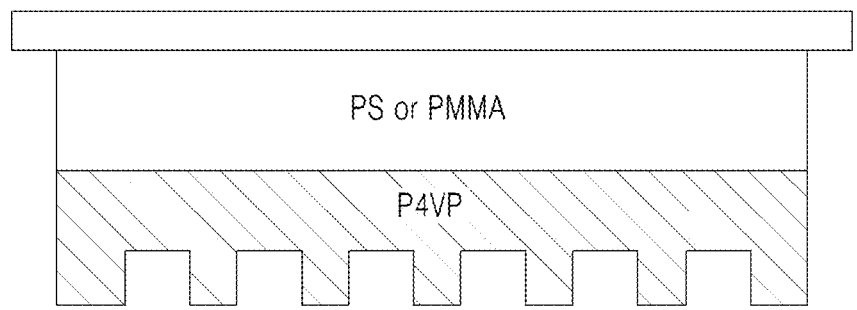
Figure 3B:
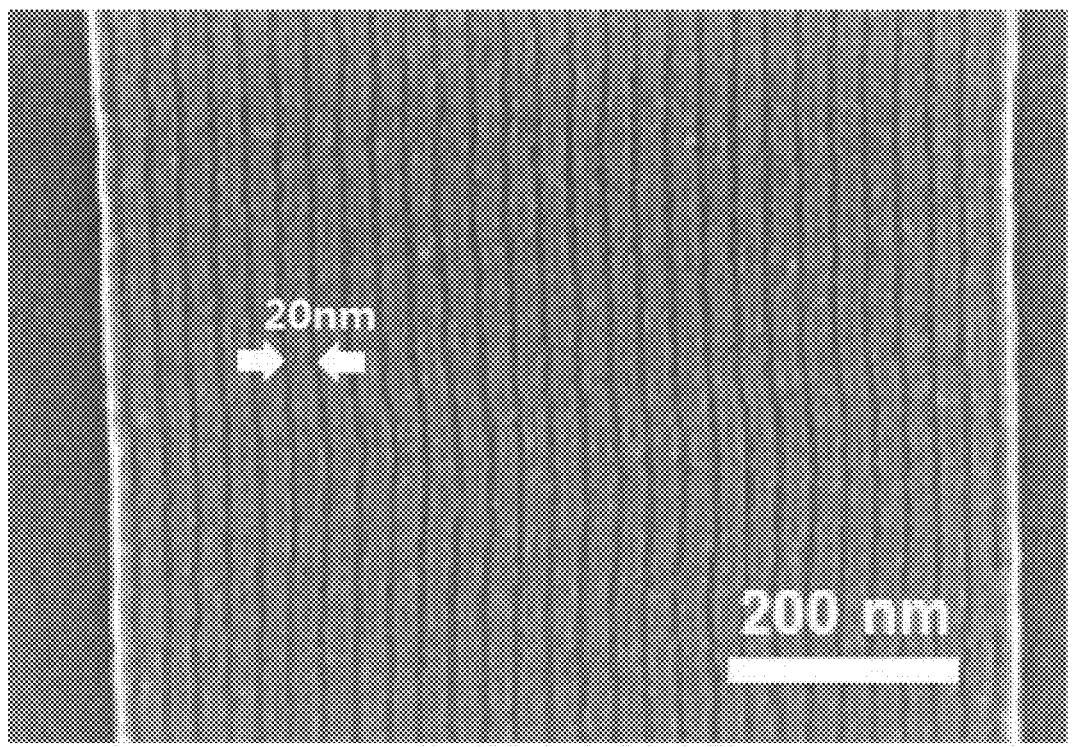
FIG. 3B shows an SEM image on a surface of a thin-film replica mold according to an embodiment of the present disclosure.
Figure 3C:
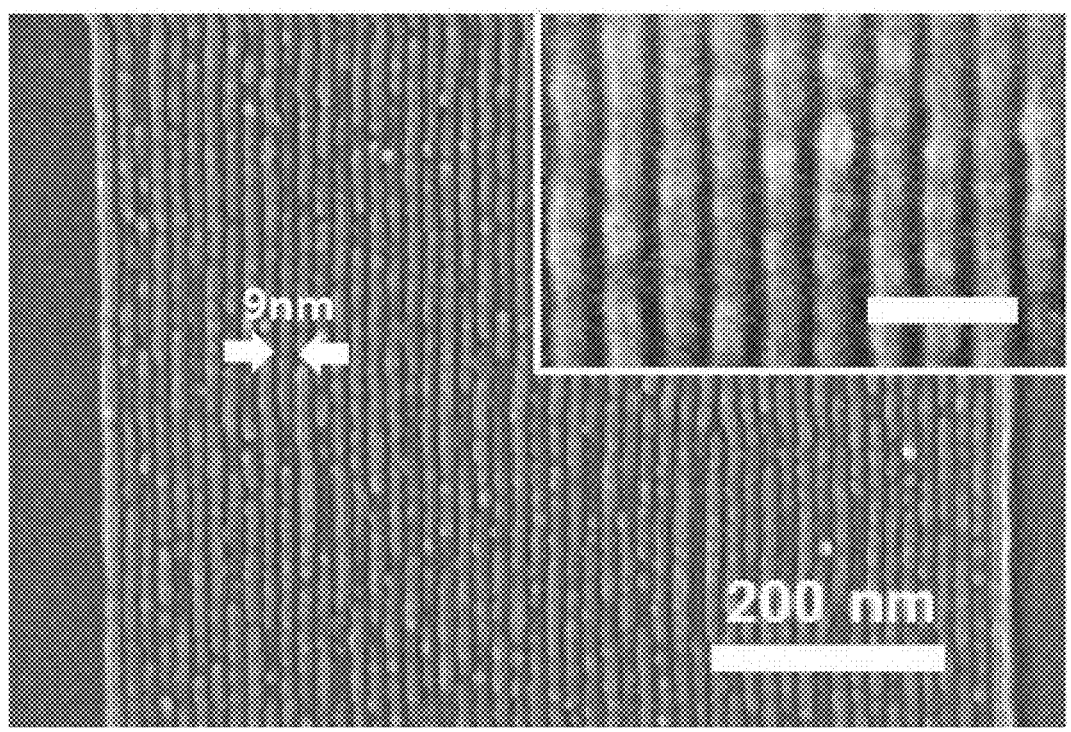
FIG. 3C shows an SEM image on a surface of a thin-film replica mold according to another embodiment of the present disclosure.

FIG. 3A is a schematic diagram illustrating a processing flow of forming a thin-film replica mold during an SERA manufacturing procedure according to an embodiment, FIG. 3B shows an SEM image on a surface of a thin-film replica mold according to an embodiment, and FIG. 3C shows an SEM image on a surface of a thin-film replica mold according to another embodiment.

Referring to FIG. 3A, an SERS device manufacturing system according to an embodiment may form a polymer thin film as a P4VP-PS multiple thin film or a P4VP-PMMA multi-layered thin film by first spreading a poly-4-vinyl pyridine (P4VP) thin film as a first thin film on a template substrate (spreading P4VP with isopropyl alcohol (IPA)) and then by spreading one of polystyrene (PS) and poly(methylmethacrylate) (PMMA) as a second thin film thereon. However, embodiments of the present disclosure may not be restrictive hereto and an SERS device manufacturing system may form a polymer thin film as a monolayered thin film by spreading one of PS and PMMA on a template substrate.

A polymer thin film coated as such may replicate a surface pattern of a template substrate, which has resolution equal to or lower than 10 nm, during a spreading process on the template substrate.

Although not shown in the drawings, an SERS device manufacturing system may use a thin-film replica mold to form a polymer thin film by separating the polymer thin film from, to which an adhesive film is attached, from a template substrate after uniformly attaching the adhesive film to a side of the polymer thin film (the counter side of the side spread on the template).

Accordingly, a thin-film replica mold manufactured through the aforementioned process may be helpful in greatly reducing a cost for materials consumed during the manufacturing procedure, and may be available in semipermanent durability because there is no need of heat treatment under high pressure and tension.

As shown in FIG. 3B for an SEM image on the surface of a thin-film replica mold of an embodiment in accordance with a line width of a surface pattern of a template substrate, the thin-film replica mold may have a linear pattern of 20 nm, or as shown in FIG. 3C for an SEM image on a thin-film replica mold of another embodiment, may have a linear pattern of 9 nm.

Figure 4A:
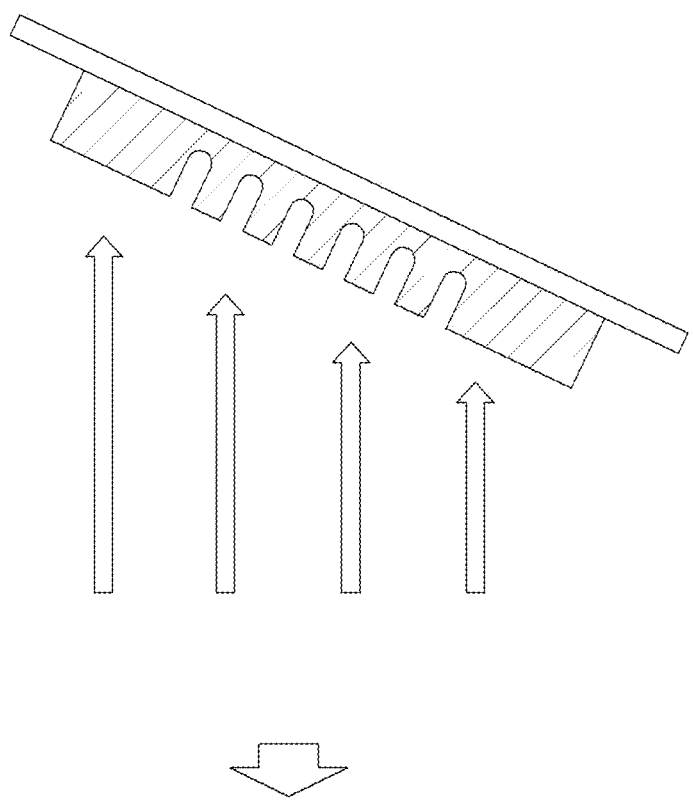
FIG. 4A is a schematic diagram illustrating a processing flow of forming nanostructures during an SERS device manufacturing procedure according to an embodiment of the present disclosure.
Figure 4A:
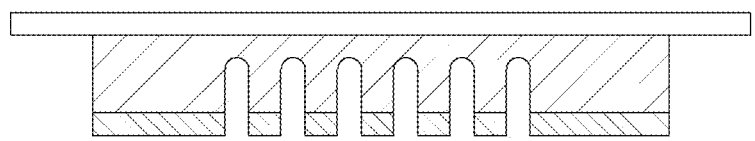
Figure 4B:
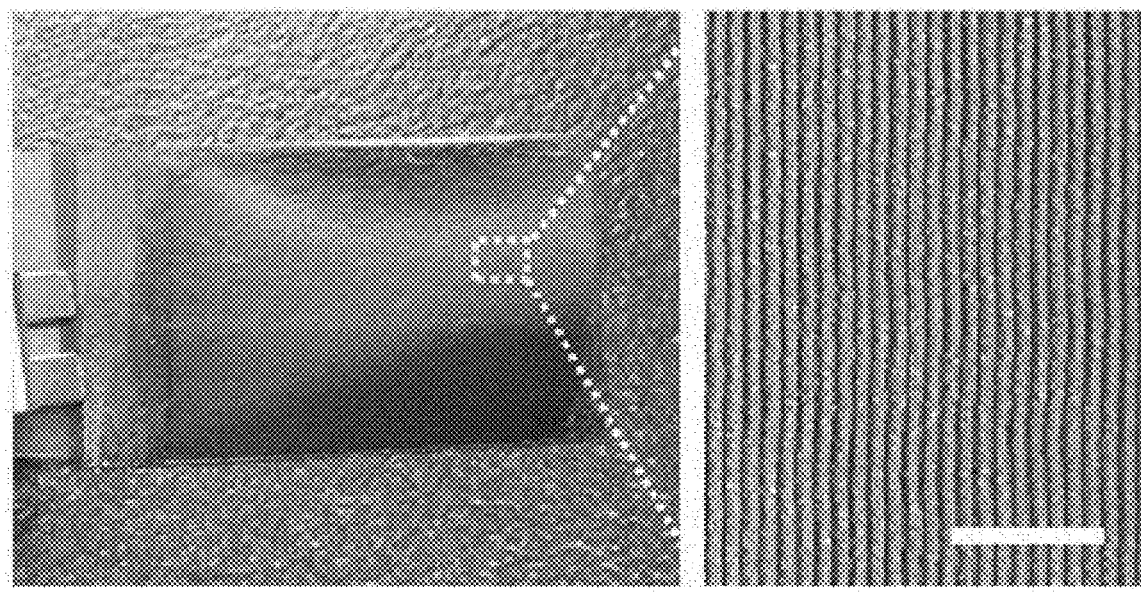
FIG. 4B shows an SEM image of nanostructures according to an embodiment of the present disclosure.

FIG. 4A is a schematic diagram illustrating a processing flow of forming nanostructures during an SERS device manufacturing procedure according to an embodiment of the present disclosure, and FIG. 4B shows an SEM image of nanostructures according to an embodiment of the present disclosure.

Referring to FIG. 4, for the purpose of depositing a functional material only on protruded parts of a surface where a thin-film replica mold is deposited, an SERS device manufacturing system according to an embodiment may deposit the functional material on the surface which is slanted with a specific angle to a direction of the deposition. For example, an SERS device manufacturing system may deposit a functional material only on protruded parts of a surface, in which a thin-film replica mold is deposited, through E-beam lithography or thermal evaporation in the condition of slanting the thin-film replica mold. In more exemplarily detail, an SERS device manufacturing system may even use a simultaneous deposition technique according to kinds of functional materials (metals such as Au, Ag, Cu, Ni, Pt, Cr, Co, or Pd). Accordingly, an SERS device manufacturing system may form nanostructures as same as a surface pattern of a thin-film replica mold in dimensions even without an additional lift-off process.

Referring to FIG. 4B showing an SEM image of nanostructures according to an embodiment, Au structures formed through the aforementioned process may be also formed by deposition Au in line width of 20 nm on a thin-film replica mold through E-beam evaporation.

As described above, nanostructures formed on a thin-film replica mold may be transferred into various target objects to manufacture various types of SERS devices. For example, in the case of transferring nanostructures into a substrate, an SERS substrate may be manufactured. In the case of transferring nanostructures into an inner surface of a vial, an SERS vial may be manufactures. In the case of transferring nanostructures into a patch-type flexible material such as PDMS which has low surface energy, an SERS patch may be manufactured.

In the case of SERS vial, as SERS nanostructures are formed on the inner surface of the vial, the Raman analysis may be performed by filling the inside of the vial with an analyzing material such as liquid and then by projecting a laser to the surface on which the nanostructures are formed. Accordingly, an SERS vial may be analyzed in the state of liquid material, different from an SERS substrate, being advantageous to the Raman analysis without exposure of harmful materials to the outside.

An SERS patch is a custom-type SERS device which is conveniently used by a user in accordance with various analyzing environments because SERS nanostructures transferred on the patch can be touched and transferred into a surface which the user desires. A polymer composing a patch for a SERS patch has low surface energy equal to or lower than 20 mJ/m$^2$, allowing SERS nanostructures of the surface to be easily transferred into various types of surfaces.

Figure 5:
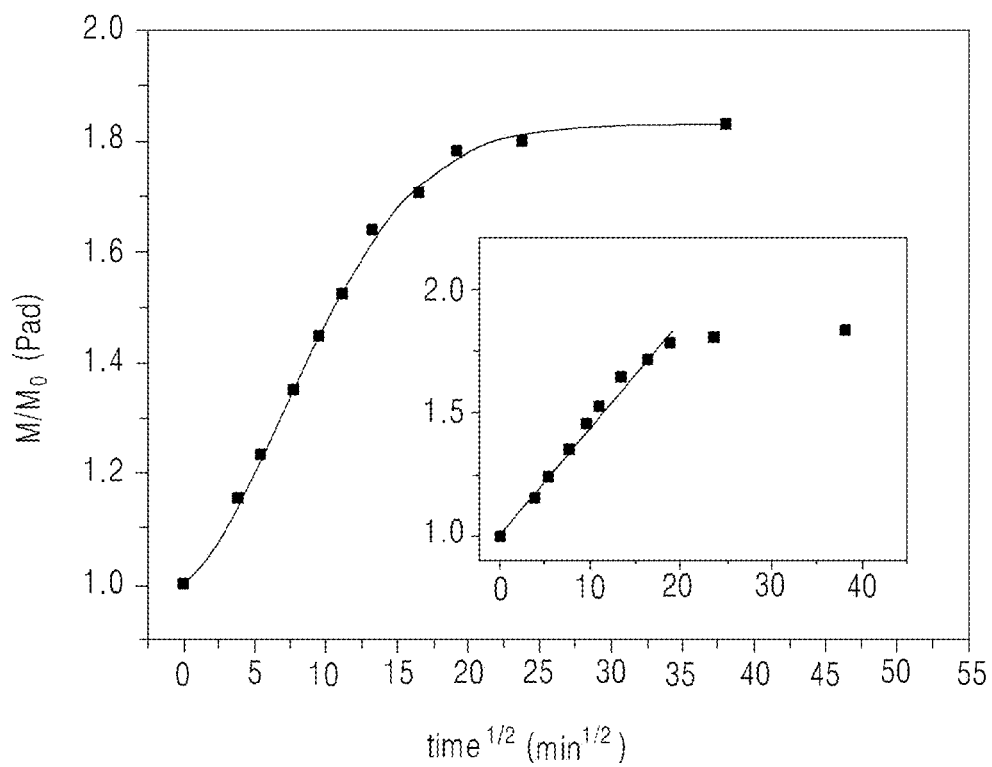
FIG. 5 is a graphic diagram showing weight variation rates along time respectively under specific conditions of temperature in the case that a polymer pad according to an embodiment of the present disclosure soaks in an organic solvent.

FIG. 5 is a graphic diagram showing weight variation rates along time respectively under specific conditions of temperature in the case that a polymer pad according to an embodiment of the present disclosure soaks in an organic solvent.

Referring to FIG. 5, in the case that a polymer pad as a PDMS pad soaks in toluene for 6 hours under the normal temperature, it can be seen that the weight thereof does not further increase after reaching the saturated expansion rate. In this regard, an SERS device manufacturing system may soak a polymer pad in an organic solvent, such as toluene, in 6 hours under the normal temperature to make the polymer pad absorb the organic solvent, and then may expand the polymer pad until the saturated expansion rate. A polymer pad manufactured as such may generate the same vapor pressure with that of pure liquid because a chemical potential of solvent molecules contained in the polymer pad is same with that of an organic solvent of the pure liquid state. Accordingly, a polymer pad containing an organic solvent may continuously emit a high-flux solvent vapor.

Figure 6:
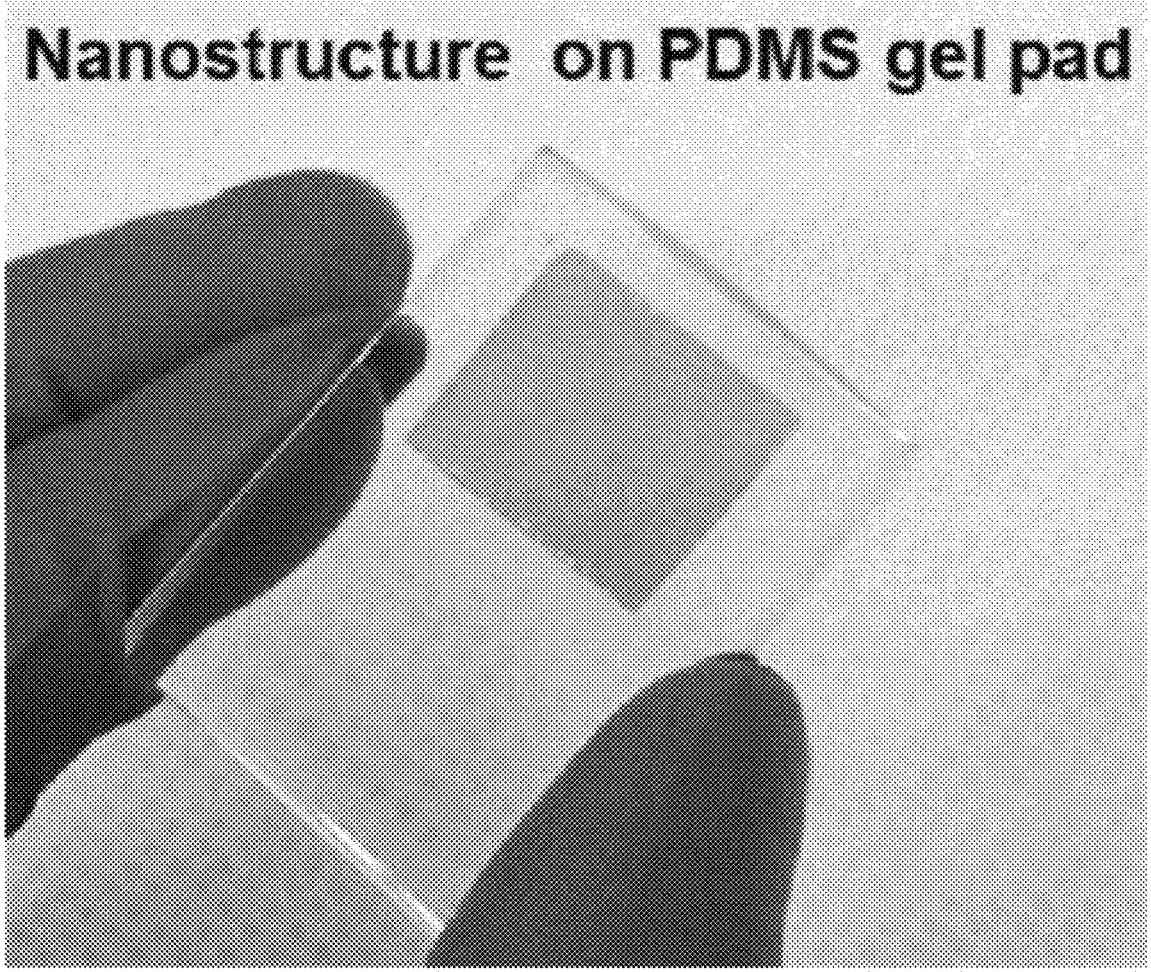
FIG. 6 shows an SEM image of a polymer pad in which nanostructures remain by a first mode of an S-nTP 2 process according to an embodiment of the present disclosure.

FIG. 6 shows an SEM image of a polymer pad in which nanostructures remain by the first mode of the S-nTP 2 process according to an embodiment of the present disclosure.

Referring to FIG. 6, an SERS device manufacturing system may leave only nanostructures on a polymer pad by performing the first mode of the S-nTP 2 process as described above. During this, a SERS device manufacturing system may remove a thin-film replica mold from a polymer pad by washing away a thin-film replica mold from the polymer pad with an organic solvent such as toluene, acetone, IPA solvent, etc., or by precipitating a polymer pad, which is touched to a thin-film replica mold, in an organic solvent, and may thereby leave only nanostructures on the polymer pad.

Additionally, in the case of a polymer thin film of a thin-film replica mold is formed of a multi-layered film, it may be permissible to remove the polymer thin film from the highest layer thereof.

Figure 7:
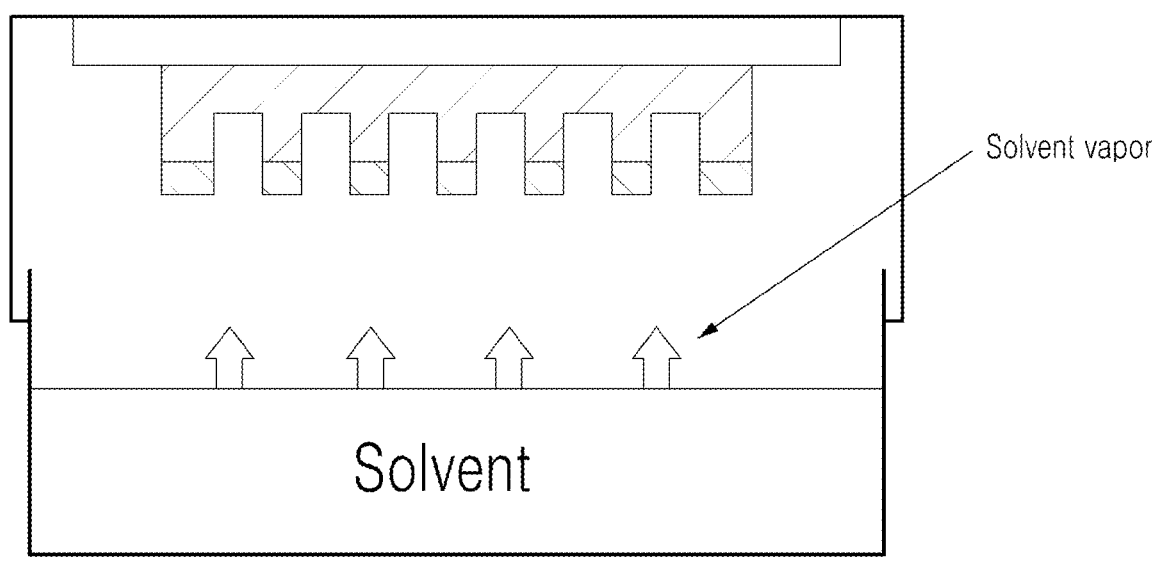
FIG. 7 is a schematic diagram illustrating a process of using an organic solvent vapor evaporated from a liquid organic solvent according to an embodiment of the present disclosure.

FIG. 7 is a schematic diagram illustrating a process of using an organic solvent vapor evaporated from a liquid organic solvent according to an embodiment of the present disclosure.

Referring to FIG. 7, an SERS device manufacturing system according to an embodiment may perform control to fill a chamber, which is fabricated to fit an area of a thin-film replica mold, with an organic solvent, to attach an adhesive film of the thin-film replica mold to a lid of the chamber, to seal the chamber, and then to inject an organic solvent vapor, which is evaporated from a liquid organic solvent in the chamber, between the adhesive film and the thin-film replica mold. The aforementioned transferring process may be performed by separating the adhesive film and the thin-film replica mold from the lid of the chamber after a specific time.

Figure 8A:
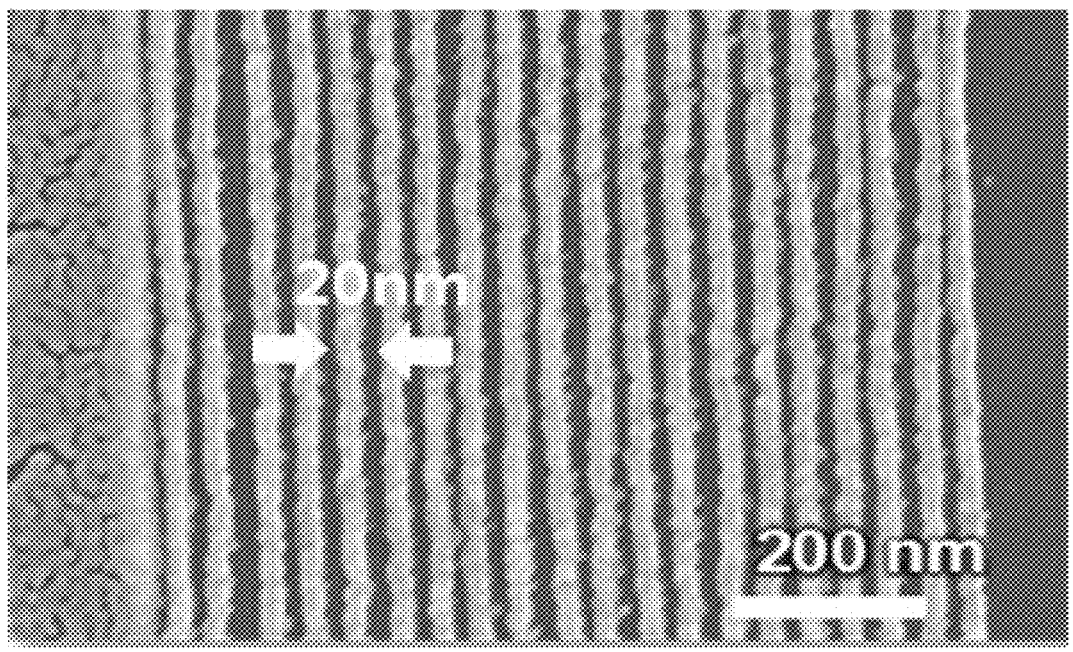
FIG. 8A shows an SEM image of an SERS substrate according to an embodiment of the present disclosure.
Figure 8B:
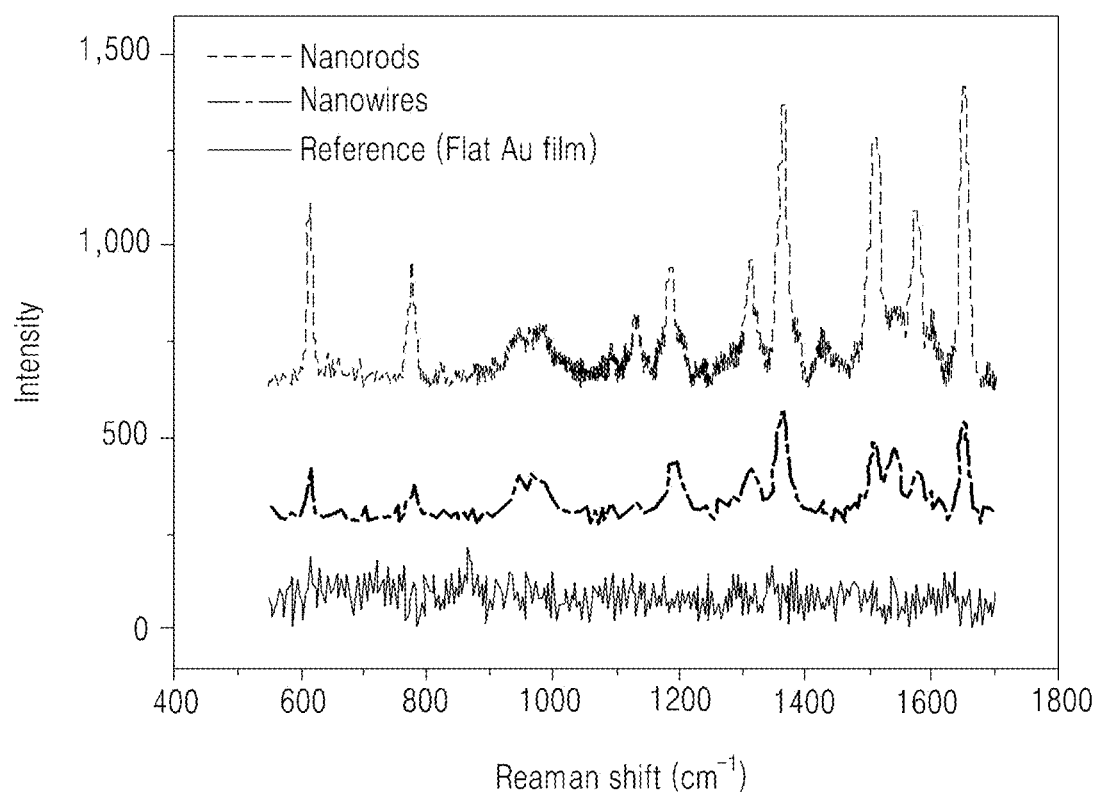
FIG. 8B is a graphic diagram showing a Raman signal of the SERS substrate of FIG. 8A.
Figure 8C:
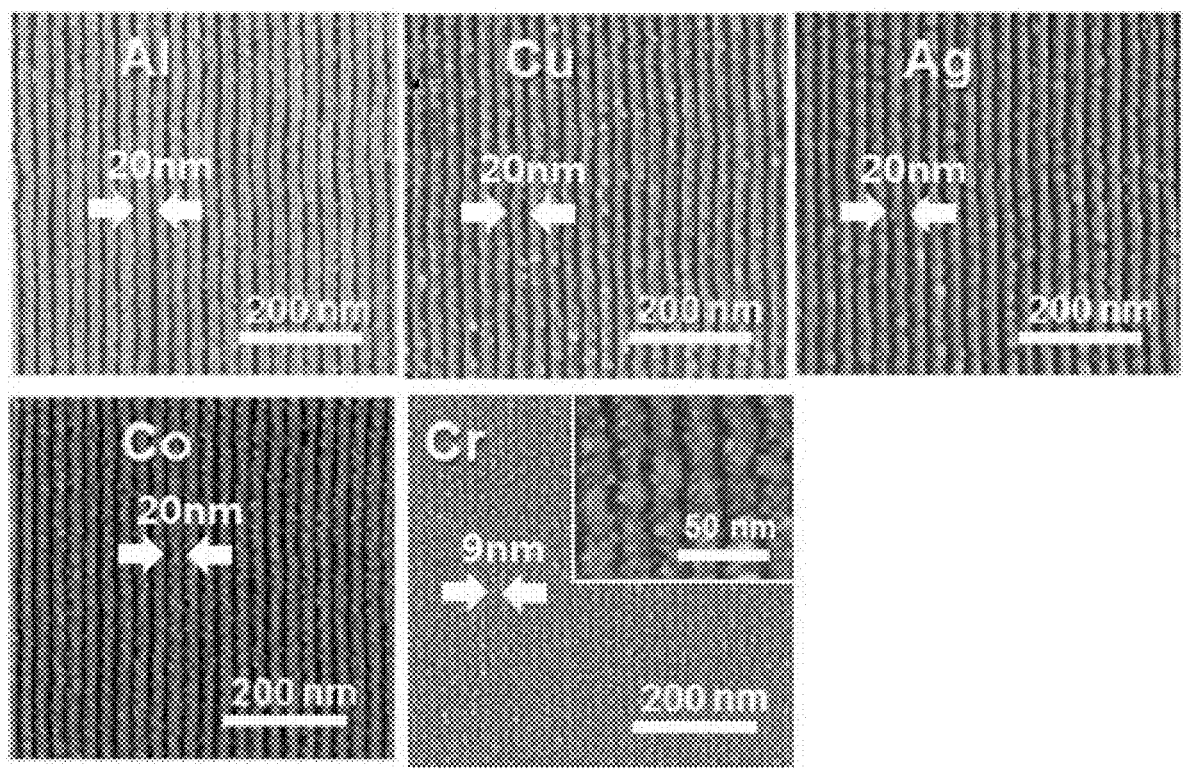
FIG. 8C shows an SEM image of an SERS substrate according to another embodiment of the present disclosure.
Figure 8D:
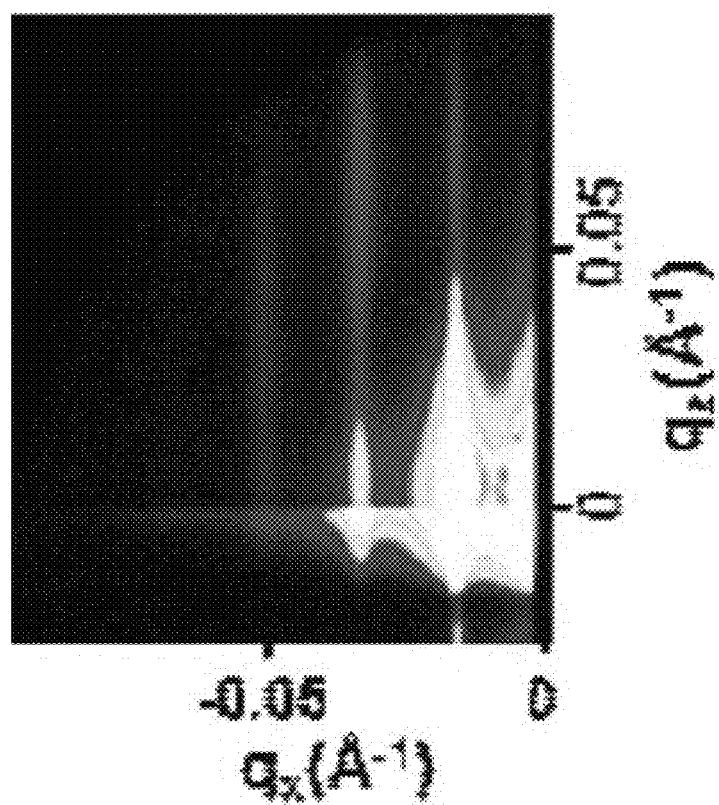
FIG. 8D shows a GISAXS pattern image of Al nanostructures included in an SERS substrate according to an embodiment of the present disclosure.

FIG. 8A shows an SEM image of an SERS substrate according to an embodiment, FIG. 8B is a graphic diagram showing a Raman signal of the SERS substrate of FIG. 8A, FIG. 8C shows an SEM image of an SERS substrate according to another embodiment, and FIG. 8D shows a GISAXS pattern image of Al nanostructures included in an SERS substrate according to an embodiment.

Referring to FIG. 8A, an SERS substrate, as an SERS device fabricated through the S-nTP 1 and S-nTP 2 processes, may be manufactured by nanotransfer-printing Au nanostructures with 20-nm line width on a substrate. A substrate into which nanostructures are transferred may be formed of at least one of metal, oxide, semiconductor, or polymer.

Such an SERS substrate may obtain a high Raman signal. For example, referring to FIG. 8B as a graph showing Raman signals from the SERS substrate of FIG. 8A, in the case of performing the Raman analysis by dripping a drop of a solution, in which Rhodamin 6G (R6G) molecules are melted, on the SERS substrate, the SERS substrate may have a strong SERS signal and SERS peaks of the SERS signal may be thus clearly noticed.

On the other hand, in the case of performing a Raman analysis by dripping a drop of a solution, in which R6G molecules are melted, on a substrate which is used with conventional Raman spectroscopy without nanostructures, the substrate used with conventional Raman spectroscopy may have a weak SERS signal and SERS peaks of an SERS signal may be accordingly unclear.

Additionally, an SERS substrate may be formed of various metallic nanostructures as well as Au nanostructures according to substances used as functional materials in the S-nTP 1 and S-nTP 2 processes. Referring to FIG. 8C showing an SEM image of an SERS substrate according to another embodiment, the SERS substrate may be manufactured to include Al nanostructures, Cu nanostructures, Ag nanostructures, Co nanostructures, of 20-nm line width, or Cr nanostructures of 9-nm line width.

As such, an SERS device manufactured through S-nTP 1 and S-nTP 2 processes according to an embodiment may be formed with aurum (Au) or argentum (Ag) nanostructures by depositing gold or silver. In the case of transferring argentum nanostructures to manufacture an SERS substrate, it may be permissible to output a higher SERS signal which is about 100 times that of aurum nanostructures.

Additionally, referring to FIG. 8D showing a GISAXS pattern image of Al nanostructures included in an SERS substrate according to an embodiment, it can be seen that the Al nanostructures included in the SERS substrate manufactured through S-nTP 1 and S-nTP 2 processes may be arranged with superior large-area alignment. Since nanostructures of an SERS device are equally formed in area based on a surface area of a template substrate, it may be allowable to implement large-area nano-wired nanostructures in the SERS device as large as the surface area of the template substrate.

Additionally, an SERS device may be manufactured in high resolution without a pretreatment process, controlling an adhesive force, and may even have a stack of nanostructured thin films through a successive nanotransfer printing process. This processing feature will be described below in conjunction with FIG. 9.

Figure 9:
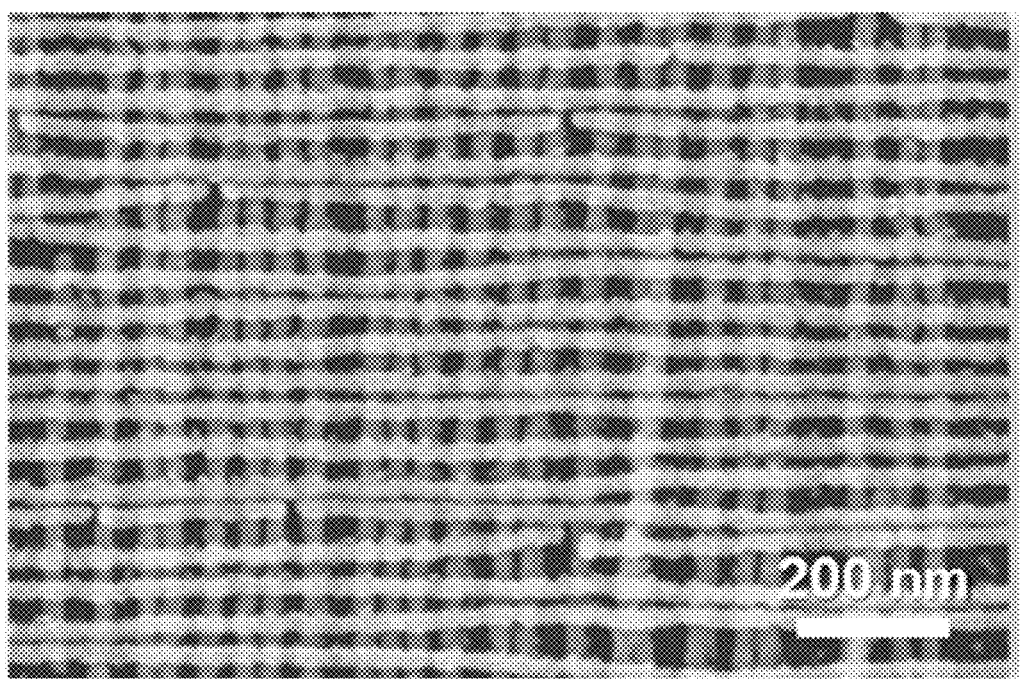
FIG. 9 shows an SEM image of a three-dimensional SERS device which is formed of stacked nanostructure thin films according to an embodiment of the present disclosure.
Figure 9:
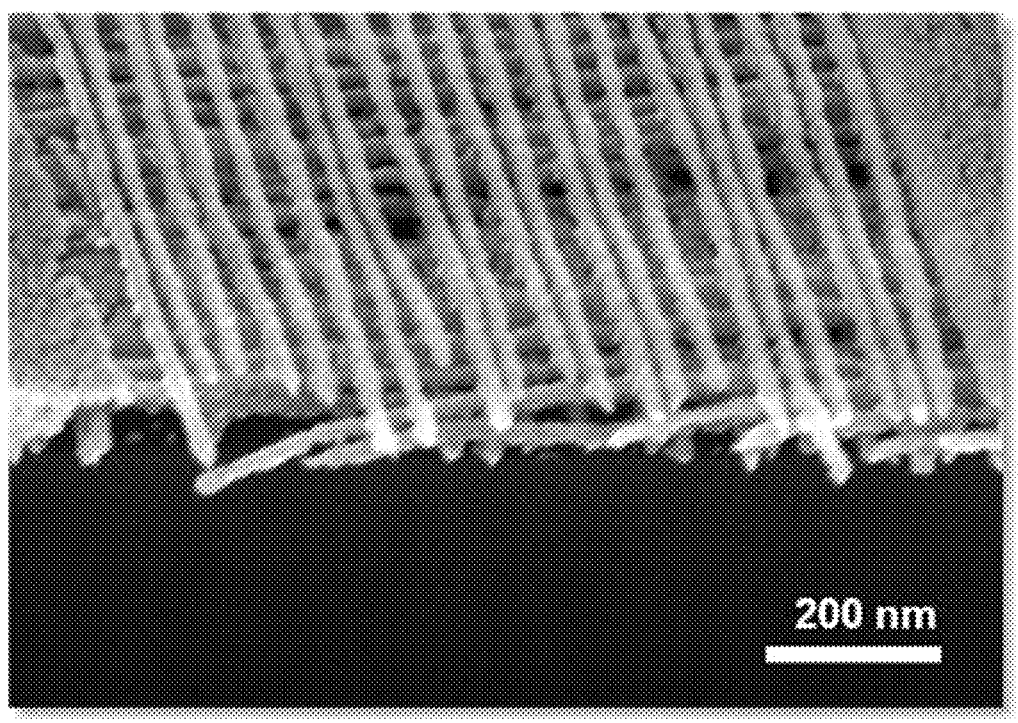
Figure 10:
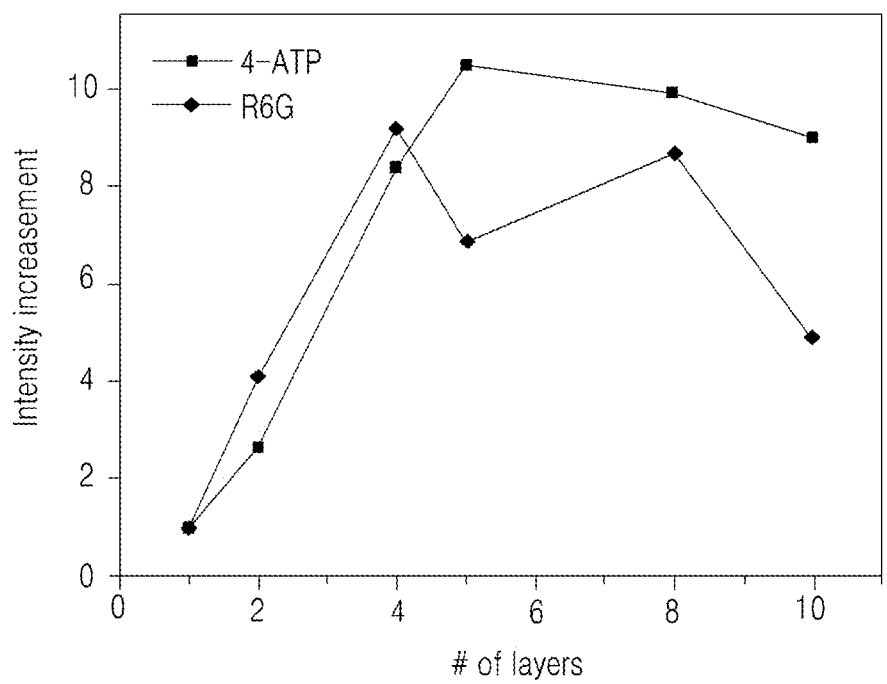
FIG. 10 is a graphic diagram showing SERS Raman signals depending on the number of the stacked nanostructure thin films of FIG. 9.

FIG. 9 shows an SEM image of a three-dimensional SERS device which is formed of stacked nanostructure thin films according to an embodiment, and FIG. 10 is a graphic diagram showing SERS Raman signals depending on the number of the stacked nanostructure thin films of FIG. 9.

Referring to FIG. 9, an SERS device according to an embodiment may be manufactured as a three-dimensional SERS device which is formed of stacked nanostructure thin films.

A three-dimensional SERS device may be manufactured by sequentially stacking nanostructured thin films on a target object through the aforementioned successive nanotransfer printing process.

For example, an SERS device manufacturing system may fabricate a cross-wired three-dimensional SERS device by transferring a first nanostructured thin film into a target object (a substrate) through a first nanotransfer printing process and then further transferring a second nanostructured film into the top of the first nanostructured thin film through a second nanotransfer printing process to intersect the first nanostructured thin film in a vertical direction. During this, the stacked nanostructure films may not be restrictive to two layers in number and may be even designed in another plurality of members (such plural nanostructured thin films may be formed to intersect each other in a vertical direction).

Accordingly, a three-dimensional SERS device having a stack of nanostructured thin films may obtain an SERS signal which greatly increases more than that of an SERS device having a monolayer of nanostructures.

For example, referring to FIG. 10 as a graphic diagram showing SERS Raman signals depending on the number of the stacked nanostructure thin films of FIG. 9, in the case of performing an SERS analysis by spreading R6G molecules with the same amount in an SERS device, it can be seen that a larger number of nanostructure thin films stacked in a three-dimensional SERS device leads an SERS Raman signal to be stronger in signal intensity.

Additionally, as described above, an SERS device manufacturing system may perform a successive nanotransfer printing process to various target objects. For example, an SERS device manufacturing system may fabricate an SERS substrate, an SERS vial, or an SERS patch by performing a successive nanotransfer printing process to a substrate, vial, or a part of food or body.

Figure 11:
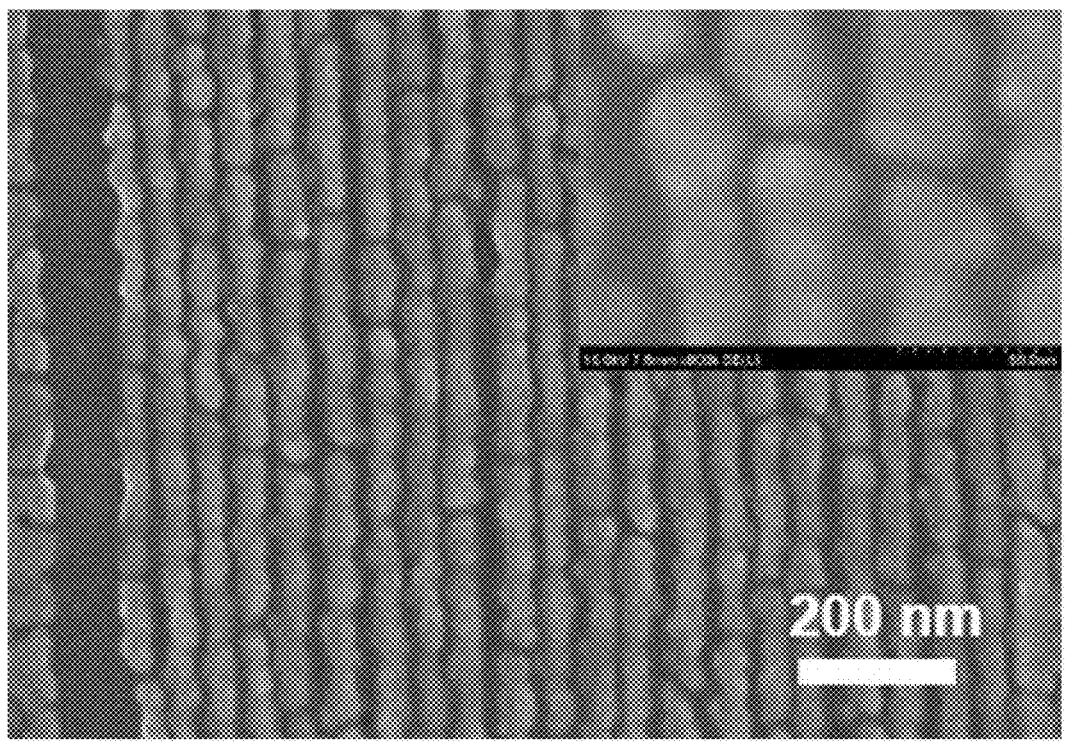
FIG. 11 shows an SEM image of a three-dimensional SERS device having a hybrid structure according to an embodiment of the present disclosure.
Figure 12:
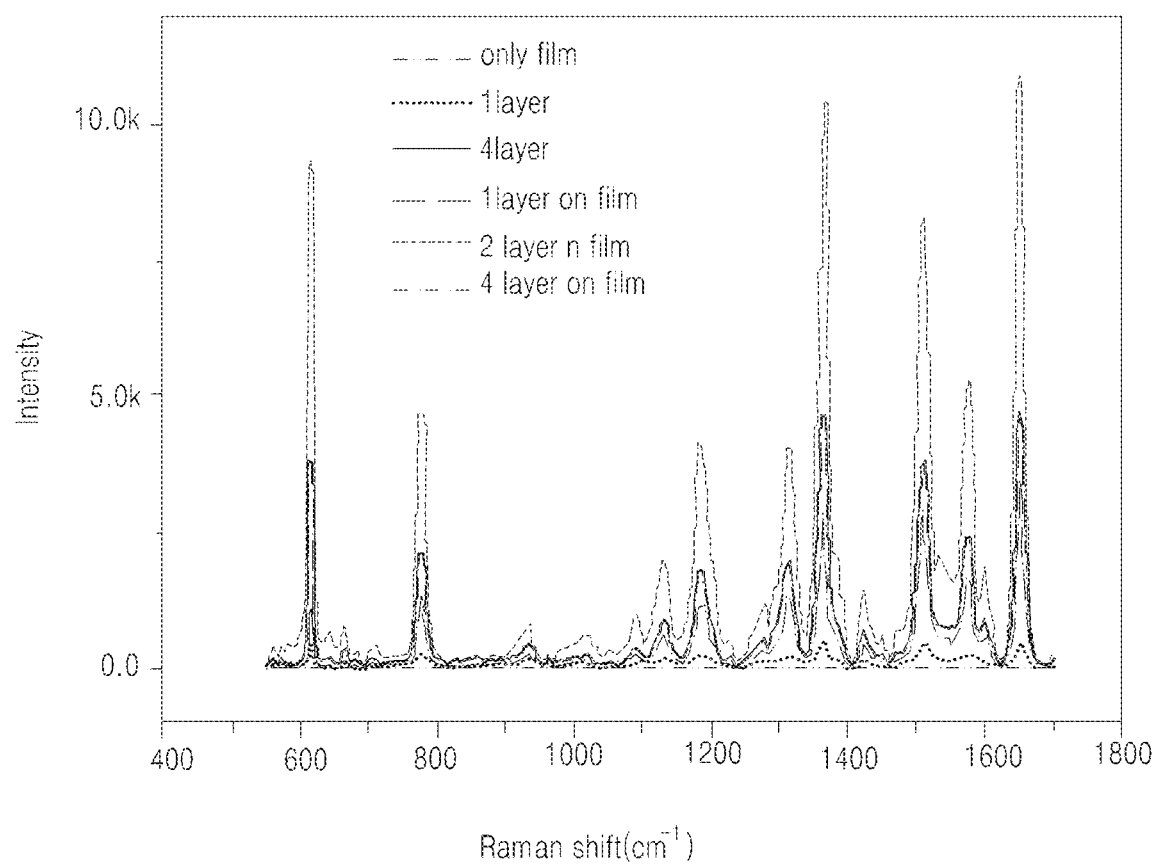
FIG. 12 is a graphic diagram showing SERS Raman signals according to the number of the stacked nanostructure thin films of FIG. 11.

FIG. 11 shows an SEM image of a three-dimensional SERS device having a hybrid structure according to an embodiment of the present disclosure, and FIG. 12 is a graphic diagram showing SERS Raman signals according to the number of the stacked nanostructure thin films of FIG. 11.

Referring to FIG. 11, an SERS device according to an embodiment may be manufactured as a three-dimensional hybrid SERS device in which nanostructures are nanotransfer-printed into a metallic thin film. This three-dimensional hybrid SERS device may have an effect of extremely strengthening a Raman signal in virtue of a plasmonic coupling phenomenon between the nanostructures and a lower metallic thin film.

For example, an SERS device manufacturing system may fabricate a three-dimensional hybrid SERS device by depositing argentum in a depth of several tens nanometers on a silicon substrate and then by transfer-printing argentine nanostructures thereon. During this, an SERS device manufacturing system may deposit nanostructures in a plurality of layers.

Referring to FIG. 12 showing SERS Raman signals according to the number of the stacked nanostructure thin films of FIG. 11, in the case of performing an SERS analysis by spreading R6G molecules with the same amount in an SERS device, it can be seen that a larger number of nanostructured layers stacked in a three-dimensional hybrid SERS device generates an effect of extremely strengthening the intensity of an SERS Raman signal.

This effect of strengthening a Raman signal may be quantified as Averaged Enhancement Factor (AEF) as shown in Table 1. Additionally, AEF may be calculated by a ratio between Raman signal intensity, which is taken from R6G molecules spread on an SERS device, and Raman signal intensity obtained from a substrate which uses a conventional technique of Raman spectroscopy without nano structures.

TABLE 1

|       | Au 1 layer | Au 4 layer | Ag 1 layer | Ag 4 layer on film | Ag 1 layer on film | Ag 2 layer on film |
|-------|------------|------------|------------|--------------------|--------------------|--------------------|
| AEF   | $2.8 \times 10^4$ | $2.6 \times 10^5$ | $1.7 \times 10^6$ | $1.5 \times 10^7$ | $1.4 \times 10^7$ | $4.1 \times 10^7$ |
| Ratio | 1          | 9.2        | 60.9       | 532                | 499                | 1437               |

Additionally, an SERS device manufacturing system may fabricate a three-dimensional hybrid SERS device which has different hybrid structures. This feature will be described below in conjunction with FIG. 13.

Figure 13:
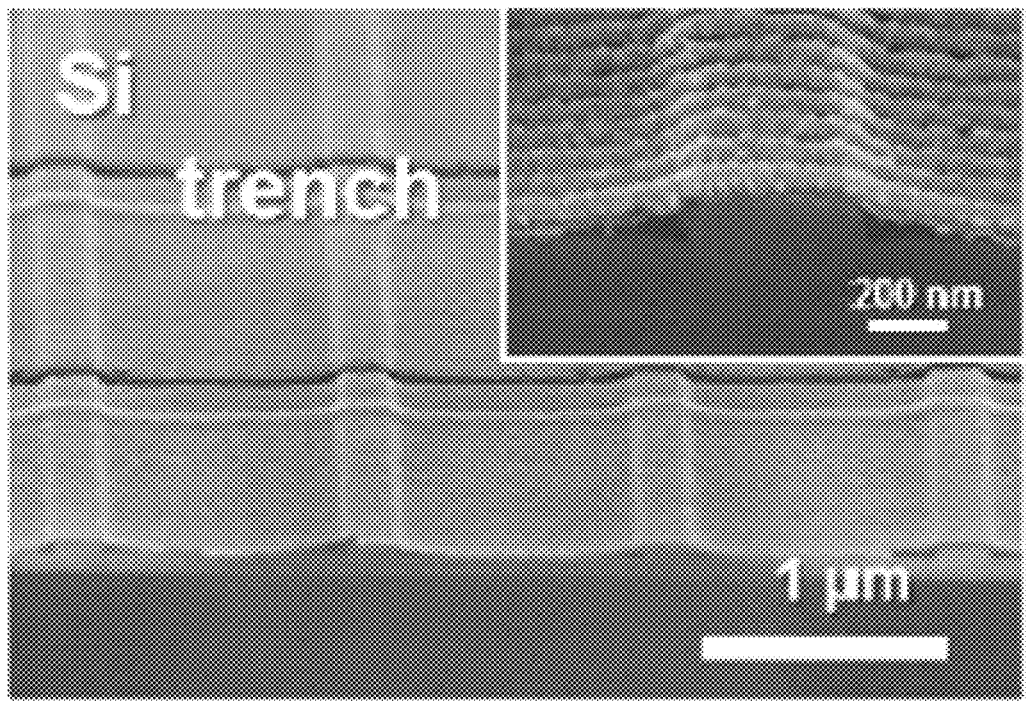
FIG. 13 shows SEM images of a three-dimensional hybrid SERS device having a hybrid structure according to another embodiment of the present disclosure.
Figure 13:
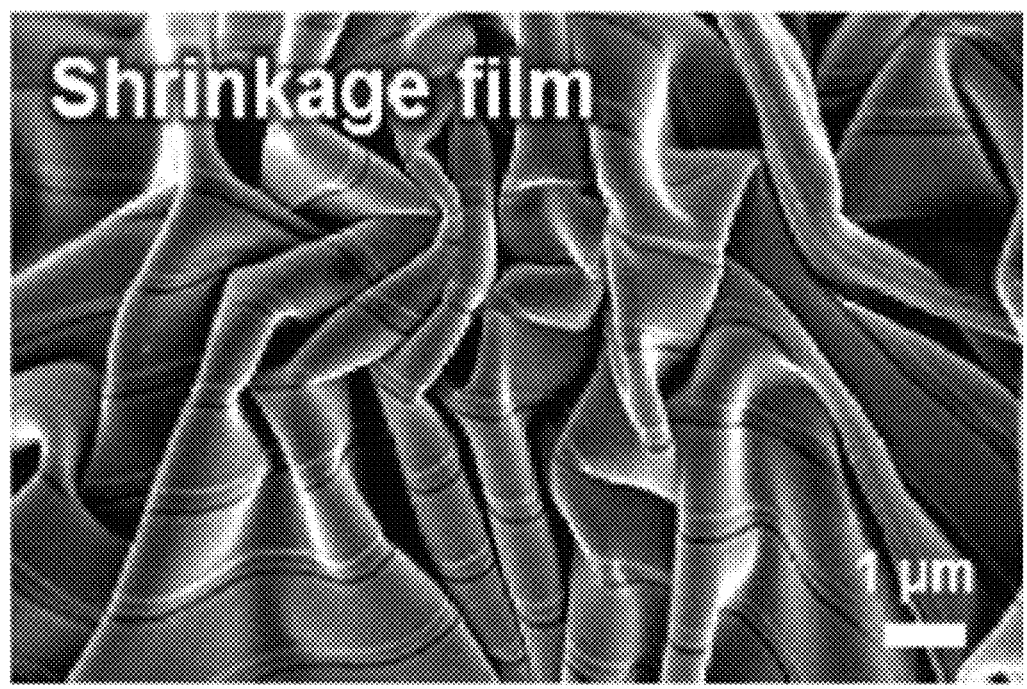

FIG. 13 shows SEM images of a three-dimensional hybrid SERS device having a hybrid structure according to another embodiment of the present disclosure.

Referring to FIG. 13, an SERS device manufacturing system according to another embodiment may fabricate a three-dimensional hybrid SERS device by printing nanostructures into a trench-type rugged silicon substrate, or by transfer-printing nanostructures into a shrinkage film.

Figure 14:
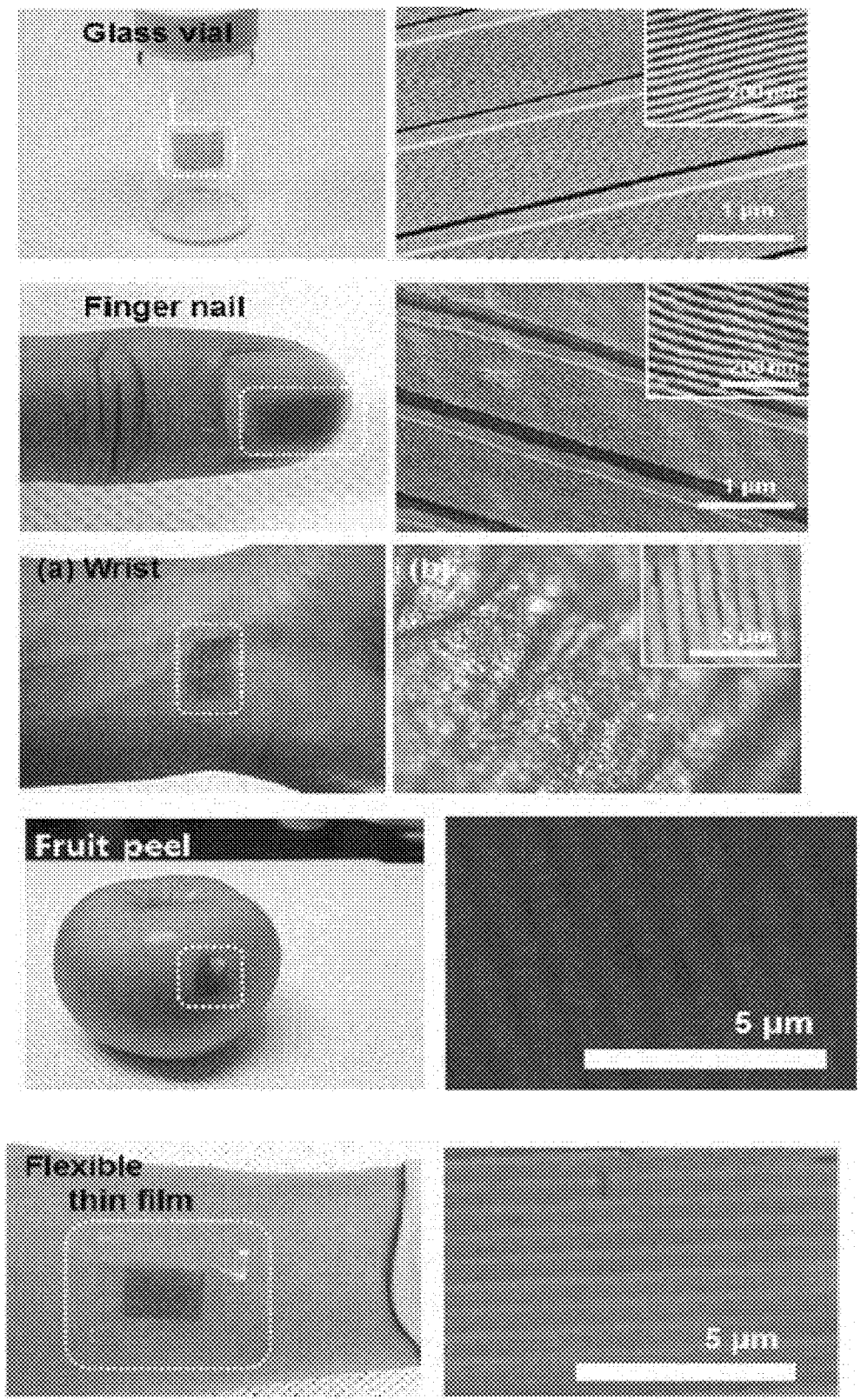
FIG. 14 shows optical images and SEM images of various SERS devices according to embodiments of the present disclosure.

FIG. 14 shows optical images and SEM images of various SERS devices according to embodiments of the present disclosure.

Referring to FIG. 14, an SERS device manufacturing system may fabricate an SERS device, which is employed to analyze ingredients of a material, by forming nanostructures of metal, such as Au, Ag, Cu, Ni, Pt, Cr, Co, or Pd, and by nanotransfer-printing the nanostructures into a target object, through the aforementioned nanotransfer printing process (the S-nTP and S-nTP processes)

For example, an SERS device manufacturing system may fabricate an SERS vial by nanotransfer-printing nanostructures into a vial, and may fabricate an SERS patch by nanotransfer-printing nanostructures into a part of body or a surface of food. Additionally, an SERS device manufacturing system may fabricate a flexible SERS substrate by nanotransfer-printing nanostructures into a flexible substrate.

While embodiments of the present disclosure have been shown and described with reference to the accompanying drawings thereof, it will be understood by those skilled in the art that various changes and modifications in form and details may be made therein without departing from the spirit and scope of the present disclosure as defined by the appended claims and their equivalents. For example, it may be allowable to achieve desired results although the embodiments of the present disclosure are preformed in other sequences different from the descriptions, and/or the elements, such as system, structure, device, circuit, and so on, are combined or assembled in other ways different from the descriptions, replaced or substituted with other elements or their equivalents.

Therefore, other implementations, other embodiments, and equivalents of the appended claims may be included in the scope of the appended claims.

What is claimed is:

1. A nanotransfer printing method comprising:
   coating a polymer thin film on a template substrate where a surface pattern is formed;
   fabricating the polymer thin film into a thin-film replica mold by using the polymer thin film and an adhesive film;
   forming nanostructures on the thin-film replica mold;
   selectively weakening an adhesive force between the adhesive film and the polymer thin film of the thin-film replica mold; and
   transferring the nanostructures onto a target object,
   wherein the selective weakening of the adhesive force between the adhesive film and the polymer thin film of the thin-film replica mold comprises:
   injecting an organic solvent vapor between the adhesive film and the polymer thin film of the thin-film replica mold to reduce interfacial detachment energy.

2. The nanotransfer printing method of claim 1, wherein the forming of the nanostructures comprises:
   depositing a functional material on the thin-film replica mold through an angled deposition.

3. The nanotransfer printing method of claim 2, wherein the depositing of the functional material on the thin-film replica mold comprises:
   depositing the functional material on the thin-film replica mold, which is slanted to have a specific angle with a surface of the thin-film replica mold that is prepared for the deposition of the thin-film replica mold in a direction of the deposition, to deposit the functional material only on protruded parts of the surface of the thin-film replica mold that is prepared for the deposition of the thin-film replica mold.

4. The nanotransfer printing method of claim 1, wherein the template substrate is formed with a rugged type of the surface pattern through a reactive ion etching process and a patterning process including at least one of photolithography, block copolymer self-assembling lithography, or E-beam lithography.

5. The nanotransfer printing method of claim 1, wherein the coating of the polymer thin film comprises one of:
   spreading a monolayered thin film and forming the polymer thin film; and
   sequentially spreading a first thin film and a second thin film and forming the polymer thin film as a multilayered thin film.

6. The nanotransfer printing method of claim 1, wherein the coating of the polymer thin film comprises:
   spreading the polymer thin film through at least one of spin coating, deep coating, or spray coating.

7. The nanotransfer printing method of claim 1, wherein the fabricating of the polymer thin film into the thin-film replica mold comprises:
   uniformly attaching the adhesive film to a side of the polymer thin film; and
   separating the polymer thin film, to which the adhesive film is attached, from the template substrate.

8. The nanotransfer printing method of claim 1, wherein the injecting of the organic solvent vapor between the adhesive film and the polymer thin film of the thin-film replica mold comprises one of:
   touching a polymer pad, which contains an organic solvent, to the polymer thin film of the thin-film replica mold and providing the organic solvent vapor; and
   providing the organic solvent vapor that is evaporated from a liquid organic solvent.

9. The nanotransfer printing method of claim 8, wherein the organic solvent has a solubility parameter that is similar to that of at least one of the polymer thin film or the adhesive film.

10. The nanotransfer printing method of claim 1, wherein the transferring of the nanostructures onto the target object comprises:
    touching the adhesive film and the thin-film replica mold, in which the nanostructures are formed, to the target object to make the nanostructures meet the target object; and
    separating the thin-film replica mold and the adhesive film from the target object to make the nanostructures transferred onto the target object.

11. The nanotransfer printing method of claim 10, wherein the separating of the thin-film replica mold and the adhesive film from the target object comprises:
    separating the adhesive film from the thin-film replica mold that is touched to the target object; and
    using an organic solvent to remove the thin-film replica mold that is touched to the target object.

12. The nanotransfer printing method of claim 1, further comprising:
    repeating the transferring of the nanostructures onto the target object to generate a three-dimensional nanostructured SERS device with a stack of a plurality of layers.

13. The nanotransfer printing method of claim 1, wherein the transferring of the nanostructures onto the target object further comprises:
    transferring the nanostructures onto a metallic thin film.

14. A nanotransfer printing method comprising:
    coating a polymer thin film on a template substrate where a surface pattern is formed;
    fabricating the polymer thin film into a thin-film replica mold by using the polymer thin film and an adhesive film;
    forming nanostructures on the thin-film replica mold;
    selectively weakening an adhesive force between the adhesive film and the polymer thin film of the thin-film replica mold; and
    transferring the nanostructures onto a target object,
    wherein the transferring of the nanostructures into the target object comprises:
    touching the adhesive film and the thin-film replica mold, in which the nanostructures are formed, to a polymer pad to make the nanostructures meet the polymer pad;

separating the thin-film replica mold and the adhesive film from the polymer pad to leave the nanostructures on the polymer pad;

touching the polymer pad, in which the nanostructures remain, to the target object to make the nanostructures meet the target object; and separating the polymer pad from the target object to make the nanostructures transferred onto the target object.

15. The nanotransfer printing method of claim 14, wherein the separating of the thin-film replica mold and the adhesive film from the polymer pad comprises:

separating the adhesive film from the polymer film of the thin-film replica mold that is touched to the polymer pad; and using an organic solvent to remove the thin-film replica mold that is touched to the polymer pad.

\* \* \* \* \*